(12) United States Patent
Terada et al.

(10) Patent No.: US 8,420,847 B2
(45) Date of Patent: Apr. 16, 2013

(54) BIS-PHOSPHATE COMPOUND AND ASYMMETRIC REACTION USING THE SAME

(75) Inventors: Masahiro Terada, Sendai (JP); Norie Momiyama, Sendai (JP); Tohru Konno, Sendai (JP)

(73) Assignees: National University Corporation Tohoku University, Sendai-shi (JP); API Corporation, Tokyo (JP)

( * ) Notice: Subject to any disclaimer, the term of this patent is extended or adjusted under 35 U.S.C. 154(b) by 0 days.

(21) Appl. No.: 13/583,875

(22) PCT Filed: Mar. 8, 2011

(86) PCT No.: PCT/JP2011/055296
§ 371 (c)(1),
(2), (4) Date: Sep. 10, 2012

(87) PCT Pub. No.: WO2011/111677
PCT Pub. Date: Sep. 15, 2011

(65) Prior Publication Data
US 2012/0330038 A1 Dec. 27, 2012

(30) Foreign Application Priority Data
Mar. 9, 2010 (JP) ................. 2010-051973

(51) Int. Cl.
*C07F 9/6574* (2006.01)

(52) U.S. Cl.
USPC .......................................... 558/79

(58) Field of Classification Search ............ 558/79
See application file for complete search history.

(56) References Cited

U.S. PATENT DOCUMENTS
2001/0031887 A1  10/2001  Inanaga

FOREIGN PATENT DOCUMENTS
JP   2001 328995   11/2001
JP   2004 149414    5/2004
WO   2005 070875    8/2005

OTHER PUBLICATIONS

Huang, W. S., et al., "From Highly Enantioselective Monomeric Catalysts to Highly Enantioselective Polymeric Catalysts: Application of Rigid and Sterically Regular Chiral Binaphthyl Polymers to the Asymmetric Synthesis of Chiral Secondary Alcohols," Journal of Organic Chemistry, vol. 64, No. 21, pp. 7940 to 7956, (1999).
Konreeva, G. A., et al., "Carbomethoxylation of propylene to methyl isobutyrate in the presence of palladium catalysts," Neftekhimiya, vol. 38, No. 4, pp. 282 to 288, (1998).
Terada, M., "Chiral Phosphoric Acids as Versatile Catalysts for Enantioselective Carbon-Carbon Bond Forming Reactions," The Chemical Society of Japan, vol. 83, No. 2, pp. 101 to 119, (2010).
Chen, X. H., et al., "Asymmetric Organocatalytic Three-Component 1,3-Dipolar Cycloaddition: Control of Stereochemistry via a Chiral BrØnsted Acid Activated Dipole," JACS Communications, J. Am. Chem. Soc., vol. 130, pp. 5652 to 5653 (2008).
Yu, J., et al., "Highly Enantioselective Catalytic 1,3-Dipolar Cycloaddition Involving 2,3-Allenoate Dipolarophiles," Organic Letter, vol. 11, No. 21, pp. 4946 to 4949, (2009).
International Search Report Issued Apr. 26, 2011 in PCT/JP11/55296 Filed Mar. 8, 2011.

*Primary Examiner* — Kristin Bianchi
(74) *Attorney, Agent, or Firm* — Oblon, Spivak, McClelland, Maier & Neustadt, L.L.P.

(57) ABSTRACT

A novel bis-phosphate compound is provided which can be applied to a wide range of reactive substrates and reactions as an asymmetric reaction catalyst and can realize an asymmetric reaction affording a high yield and a high enantiomeric excess. The bis-phosphate compound has a tetraaryl skeleton represented by General Formula (1). In an asymmetric reaction, an amidodiene and an unsaturated aldehyde compound are reacted with each other in the presence of the optically active bis-phosphate compound to give an optically active amidoaldehyde. The invention allows a reaction such as an asymmetric Diels-Alder reaction to proceed efficiently, which has been difficult with conventional mono-phosphate compounds. Thus, the invention enables an industrially feasible method for the production of optically active amidoaldehydes, optically active β-amino acid derivatives, optically active diamine compounds, optically active pyrrolidine derivatives and optically active dihydropyran derivatives which are useful as products such as medicines, agricultural chemicals and chemical products as well as synthesis intermediates for such products.

19 Claims, No Drawings

BIS-PHOSPHATE COMPOUND AND ASYMMETRIC REACTION USING THE SAME

FIELD OF INVENTION

The present invention relates to a bis-phosphate compound and an asymmetric reaction using the compound.

BACKGROUND OF INVENTION

Optically active mono-phosphate compounds have recently attracted attention as optically active Brønsted acid catalysts to catalyze asymmetric reactions represented by asymmetric Mannich reaction.

For example, Mannich reactions have been reported as one of the reactions using an optically active mono-phosphate compound as an asymmetric Brønsted acid catalyst (Patent Literature 1 and Non Patent Literature 1).

Patent Literature 1 describes a process for producing amines which includes reacting an imine compound with a nucleophilic compound in the presence of a mono-phosphate compound. In Non Patent Literature 1, N-tert-butoxycarbonyl-benzaldehyde imine and acetylacetone are reacted with each other using an optically active mono-phosphate as an asymmetric catalyst which has a bi-naphthyl skeleton as an optically active site, thus giving a β-aminoketone with a yield of 99% and an enantiomeric excess of 95% e.e. Further, Non Patent Literatures 2 and 3 describe optically active bis-phosphate compounds and asymmetric reactions using the compounds.

CITATION LIST

Patent Literature

PTL 1: International Publication No. WO 2005/070875

Non Patent Literature

NPL 1: M. Terada, Bull. Chem. Soc. Jpn. 2010, 83, p. 101-119.
NPL 2: X. -H. Chen, W. -Q. Zhang, L. -Z. Gong, J. Am. Chem. Soc. 2008, 130, P. 5652.
NPL 3: J. Yu, X. -H. Chen, J. Song. W. -J. Chen, L. -Z. Gong, Org. Lett. 2009, 11, p. 4946.

OBJECT AND SUMMARY OF INVENTION

Object of Invention

However, the fact that conventional optically active mono-phosphate compounds have only a single phosphate site limits reactive substrates and reactions to which the compounds are applicable. Thus, they are not always fully utilized in the current state of industry.

While Non Patent Literatures 2 and 3 report examples of optically active bis-phosphate compounds and asymmetric reactions using such compounds, there have been no reports of the introduction of a substituent near the functional phosphate group. Such an introduction of a substituent has not been spread to a wide range of reactions because it requires a multistage conversion reaction. Further, such a bis-phosphate compound contains two phosphate groups introduced into respective binaphthyl skeletons. Thus, similarly to the case of a conventional mono-phosphate, the binaphthyl skeleton and the functional phosphate group have a one to one relationship. Furthermore, these two functional phosphate groups are distant from each other. Because of such a positional relationship, a strong interaction cannot be expected to work between the two functional phosphate groups. From the foregoing, conventional optically active bis-phosphate compounds too have been disclosed to be applicable to limited reactive substrates and reactions, and are not always fully utilized in the current state of industry.

The present invention has been made in view of the conventional circumstances described above. It is therefore an object of the invention to provide a novel bis-phosphate compound which can be applied to a wide range of reactive substrates and reactions as an asymmetric reaction catalyst and can realize an asymmetric reaction affording a high yield and a high enantiomeric excess, as well as to provide an asymmetric reaction using the bis-phosphate compound.

Summary of Invention

The present inventors carried out studies in order to solve problems described above. As a result, the present inventors have found that a bis-phosphate compound having a tetraaryl skeleton, in particular a novel optically active bis-phosphate compound having axial chirality functions as an effective catalyst in various asymmetric reactions such as asymmetric Mannich reactions, asymmetric aza-ene type reactions, asymmetric hetero Diels-Alder reactions, asymmetric Friedel-Crafts reactions or asymmetric Diels-Alder reactions. The present invention has been completed based on the finding.

That is, the following inventions are provided according to the present invention.

[1] A bis-phosphate compound represented by Formula (1) below:

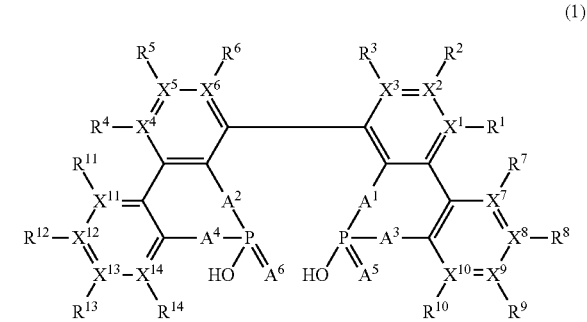

(1)

wherein $R^1$ to $R^{14}$ each independently represent a hydrogen atom, an optionally substituted hydrocarbon group, an optionally substituted heterocyclic group, a hydroxyl group, an optionally substituted alkoxy group, an optionally substituted aryloxy group, an optionally substituted acyl group, an optionally substituted alkoxycarbonyl group, an optionally substituted aryloxycarbonyl group, an optionally substituted carbamoyl group, an optionally substituted alkylthiocarbonyl group, an optionally substituted arylthiocarbonyl group, a carboxyl group, an optionally substituted alkylthio group, an optionally substituted arylthio group, an optionally substituted amino group, a substituted silyl group or a halogen atom; in any combination of $R^1$ to $R^{14}$, these substituents may be linked together to form a ring; $X^1$ to $X^{14}$ each independently represent a carbon atom or a nitrogen atom wherein in the case of a nitrogen atom, there is no substituent on the nitrogen atom; $A^1$ to $A^6$ each independently represent an oxygen atom or a sulfur atom; and the —OH group in the phosphate moiety may form a metal salt, an ammonium salt or an amine salt.

[2] The bis-phosphate compound described in [1], which is optically active.

[3] The bis-phosphate compound described in [2], which is an optically active compound having axial chirality.

[4] An asymmetric reaction performed in the presence of the optically active bis-phosphate compound described in [2] or [3].

[5] The asymmetric reaction described in [4], in which an amidodiene and an unsaturated aldehyde compound are reacted with each other in the presence of the optically active bis-phosphate compound described in [2] or [3] to produce an optically active amidoaldehyde.

[6] The asymmetric reaction described in [4], in which an imine and a 1,3-diketone are reacted with each other in the presence of the optically active bis-phosphate compound described in [2] or [3] to produce an optically active β-aminoketone.

[7] The asymmetric reaction described in [4], in which an imine and a furan are reacted with each other in the presence of the optically active bis-phosphate compound described in [2] or [3] to produce an optically active furanylamine.

[8] The asymmetric reaction described in [4], in which an imine and a carbamate are reacted with each other in the presence of the optically active bis-phosphate compound described in [2] or [3] to produce an optically active β-aminoketone.

[9] A method for producing the bis-phosphate compound in any one of [1] to [3], including reacting a compound represented by General Formula (N) below with a phosphorylating agent:

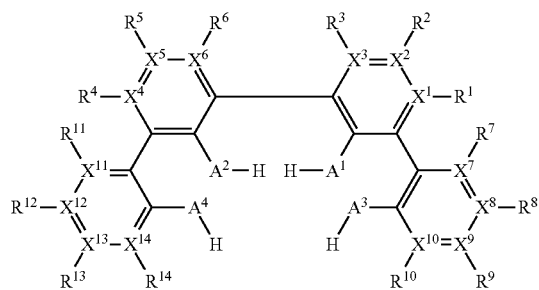

(N)

wherein $R^1$ to $R^{14}$, $X^1$ to $X^{14}$, and $A^1$ to $A^4$ are the same as defined in General Formula (1).

[10] The method for producing the bis-phosphate compound described in [9], wherein the phosphorylating agent is one, or two or more selected from the group consisting of phosphorus oxyhalides, phosphorus halides, dihalogenophosphines and thiophosphoryl halides.

Advantageous Effects of Invention

The present invention can provide a bis-phosphate compound having a tetraaryl skeleton and represented by General Formula (1) which is useful as a catalyst for various asymmetric reactions. Further, according to the invention, various asymmetric reactions such as asymmetric Mannich reactions, asymmetric aza-ene type reactions, asymmetric hetero Diels-Alder reactions, asymmetric Friedel-Crafts reactions or asymmetric Diels-Alder reactions are allowed to proceed efficiently by the use of the bis-phosphate compound.

In particular, the present invention allows an asymmetric Diels-Alder reaction to proceed efficiently, which has been difficult with conventional mono-phosphate compounds and conventional bis-phosphate compounds. Thus, the invention enables an industrially feasible method for the production of optically active amidoaldehydes, optically active β-amino acid derivatives, optically active diamine compounds, optically active pyrrolidine derivatives, optically active dihydropyran derivatives and optically active amidoaldehyde derivatives which are useful as products such as medicines, agricultural chemicals and chemical products as well as synthesis intermediates for such products. The bis-phosphate compound of the invention permits a substituent to be easily introduced near the functional phosphate group. Further, such an introduction of a substituent can be made by a short-stage conversion reaction. Thus, the compound is excellent from the viewpoint of creating asymmetric reaction fields in accordance with a various kinds of reaction systems. Because two functional phosphate groups can be introduced with one chiral source of the bi-naphthyl skeleton, the chiral source of the bi-naphthyl skeleton can be effectively utilized. Further, the two functional phosphate groups are close to each other and their interaction can be expected to produce synergetic effects for the compound to function as a chiral Brønsted acid catalyst based on a higher acidity. The above-described advantageous effects are probably ascribed to this fact.

DESCRIPTION OF EMBODIMENTS

Embodiments of the present invention will be described in detail hereinbelow.

[Bis-phosphate Compound]

A bis-phosphate compound according to the present invention is represented by General Formula (1) below:

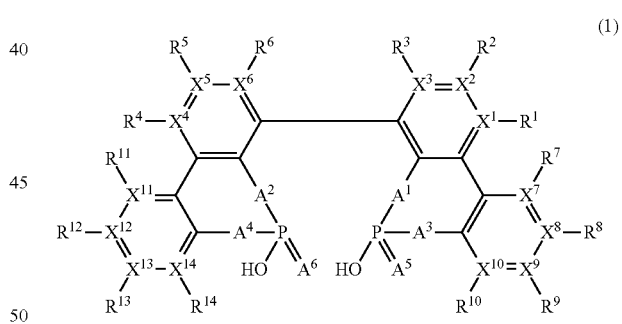

(1)

In the formula, $R^1$ to $R^{14}$ each independently represent a hydrogen atom, an optionally substituted hydrocarbon group, an optionally substituted heterocyclic group, a hydroxyl group, an optionally substituted alkoxy group, an optionally substituted aryloxy group, an optionally substituted acyl group, an optionally substituted alkoxycarbonyl group, an optionally substituted aryloxycarbonyl group, an optionally substituted carbamoyl group, an optionally substituted alkylthiocarbonyl group, an optionally substituted arylthiocarbonyl group, a carboxyl group, an optionally substituted alkylthio group, an optionally substituted arylthio group, an optionally substituted amino group, a substituted silyl group or a halogen atom. In any combination of $R^1$ to $R^{14}$, these substituents may be linked together to form a ring. $X^1$ to $X^{14}$ each independently represent a carbon atom or a nitrogen atom; in the case of a nitrogen atom, there is no substituent on the nitrogen atom. $A^1$ to $A^6$ each independently represent an oxygen atom or a sulfur atom. The —OH group in the phosphate moiety may form a metal salt, an ammonium salt or an amine salt.

[1] $R^1$ to $R^{14}$

In General Formula (1), $R^1$ to $R^{14}$ each independently represent a hydrogen atom, an optionally substituted hydrocarbon group, an optionally substituted heterocyclic group, a hydroxyl group, an optionally substituted alkoxy group, an optionally substituted aryloxy group, an optionally substituted acyl group, an optionally substituted alkoxycarbonyl group, an optionally substituted aryloxycarbonyl group, an optionally substituted carbamoyl group, an optionally substituted alkylthiocarbonyl group, an optionally substituted arylthiocarbonyl group, a carboxyl group, an optionally substituted alkylthio group, an optionally substituted arylthio group, an optionally substituted amino group, a substituted silyl group or a halogen atom. In any combination of $R^1$ to $R^{14}$, these substituents may be linked together to form a ring.

{Optionally Substituted Hydrocarbon Groups}

Examples of the optionally substituted hydrocarbon groups represented by $R^1$ to $R^{14}$ include alkyl groups, alkenyl groups, alkynyl groups and aryl groups.

<Alkyl Groups>

The alkyl groups represented by $R^1$ to $R^{14}$ may be linear, branched or cyclic.

Preferred examples of the alkyl groups include linear, branched or cyclic alkyl groups having 1 to 20 carbon atoms, preferably 1 to 10 carbon atoms, and more preferably 1 to 6 carbon atoms. Specific examples include linear or branched alkyl groups such as methyl group, ethyl group, n-propyl group, isopropyl group, n-butyl group, sec-butyl group, isobutyl group, tert-butyl group, n-pentyl group, neopentyl group, tert-pentyl group, hexyl group, heptyl group, octyl group, nonyl group, decyl group, cetyl group and stearyl group; and cycloalkyl groups such as cyclopentyl group, methylcyclopentyl group, cyclohexyl group, methylcyclohexyl group and cyclooctyl group.

<Substituents for Alkyl Groups>

These alkyl groups may optionally have a substituent. Examples of the substituents include hydrocarbon groups, aliphatic heterocyclic groups, aromatic heterocyclic groups, alkoxy groups, alkylenedioxy groups, aryloxy groups, aralkyloxy groups, heteroaryloxy groups, alkylthio groups, arylthio groups, aralkylthio groups, heteroarylthio groups, amino group, substituted amino groups, cyano group, hydroxyl group, oxo group, nitro group, mercapto group, tri-substituted silyl groups and halogen atoms.

Examples of the hydrocarbon groups which substitute the alkyl groups include alkyl groups, alkenyl groups, alkynyl groups, aryl groups and aralkyl groups.

The alkyl groups which substitute the alkyl groups may be linear, branched or cyclic. For example, linear, branched or cyclic alkyl groups having 1 to 20 carbon atoms are preferable. Specific examples include linear or branched alkyl groups such as methyl group, ethyl group, n-propyl group, isopropyl group, n-butyl group, sec-butyl group, isobutyl group, tert-butyl group, n-pentyl group, neopentyl group, tert-pentyl group, hexyl group, heptyl group, octyl group, nonyl group, decyl group, cetyl group and stearyl group; and cycloalkyl groups such as cyclopentyl group, cyclohexyl group and cyclooctyl group.

The alkenyl groups which substitute the alkyl groups may be linear or branched. Examples thereof include alkenyl groups having 2 to 15 carbon atoms, preferably 2 to 10 carbon atoms, and more preferably 2 to 6 carbon atoms. Specific examples include ethenyl group, propenyl group, 1-butenyl group, pentenyl group and hexenyl group.

The alkynyl groups which substitute the alkyl groups may be linear or branched. Examples thereof include alkynyl groups having 2 to 15 carbon atoms, preferably 2 to 10 carbon atoms, and more preferably 2 to 6 carbon atoms. Specific examples include ethynyl group, 1-propynyl group, 2-propynyl group, 1-butynyl group, 3-butynyl group, pentynyl group and hexynyl group.

Examples of the aryl groups which substitute the alkyl groups include aryl groups having 6 to 20 carbon atoms. Specific examples include phenyl group, naphthyl group, anthryl group, phenanthryl group, biphenyl group and terphenyl group.

Examples of the aralkyl groups which substitute the alkyl groups include groups corresponding to the aforementioned alkyl groups except that at least one hydrogen atom has been substituted with any of the aforementioned aryl groups. For example, aralkyl groups having 7 to 12 carbon atoms are preferable. Specific examples include benzyl group, 2-phenylethyl group, 1-phenylpropyl group and 3-naphthylpropyl group.

Examples of the aliphatic heterocyclic groups which substitute the alkyl groups include 5- to 8-membered, preferably 5- or 6-membered monocyclic aliphatic heterocyclic groups, or polycyclic or condensed ring aliphatic heterocyclic groups which each have 2 to 14 carbon atoms and at least 1, preferably 1 to 3 heteroatoms such as nitrogen atoms, oxygen atoms and sulfur atoms. Specific examples of the aliphatic heterocyclic groups include pyrrolidyl-2-one group, piperidino group, piperadinyl group, morpholino group, tetrahydrofuryl group, tetrahydropyranyl group and tetrahydrothienyl group.

Examples of the aromatic heterocyclic groups which substitute the alkyl groups include 5- to 8-membered, preferably 5- or 6-membered monocyclic heteroaryl groups, or polycyclic or condensed ring heteroaryl groups which each have 2 to 15 carbon atoms and at least 1, preferably 1 to 3 heteroatoms such as nitrogen atoms, oxygen atoms and sulfur atoms. Specific examples thereof include furyl group, thienyl group, pyridyl group, pyrimidyl group, pyrazyl group, pyridazyl group, pyrazolyl group, imidazolyl group, oxazolyl group, thiazolyl group, benzofuryl group, benzothienyl group, quinolyl group, isoquinolyl group, quinoxalyl group, phthalazyl group, quinazolyl group, naphthylidyl group, cinnolyl group, benzimidazolyl group, benzoxazolyl group and benzothiazolyl group.

The alkoxy groups which substitute the alkyl groups may be linear, branched or cyclic. Examples thereof include alkoxy groups having 1 to 6 carbon atoms. Specific examples include methoxy group, ethoxy group, n-propoxy group, isopropoxy group, n-butoxy group, 2-butoxy group, isobutoxy group, tert-butoxy group, n-pentyloxy group, 2-methylbutoxy group, 3-methylbutoxy group, 2,2-dimethylpropyloxy group, n-hexyloxy group, 2-methylpentyloxy group, 3-methylpentyloxy group, 4-methylpentyloxy group, 5-methylpentyloxy group, cyclohexyloxy group, methoxymethoxy group and 2-ethoxyethoxy group.

Examples of the alkylenedioxy groups which substitute the alkyl groups include alkylenedioxy groups having 1 to 3 carbon atoms. Specific examples include methylene dioxy group, ethylenedioxy group, trimethylenedioxy group, propylenedioxy group and isopropylidenedioxy group.

Examples of the aryloxy groups which substitute the alkyl groups include aryloxy groups having 6 to 14 carbon atoms. Specific examples include phenoxy group, tolyloxy group, xylyloxy group, naphthoxy group and anthryloxy group.

Examples of the aralkyloxy groups which substitute the alkyl groups include aralkyloxy groups having 7 to 12 carbon atoms. Specific examples include benzyloxy group, 4-methoxyphenylmethoxy group, 1-phenylethoxy group, 2-phenylethoxy group, 1-phenylpropoxy group, 2-phenylpropoxy group, 3-phenylpropoxy group, 1-phenylbutoxy group, 3-phenylbutoxy group, 4-phenylbutoxy group, 1-phenylpentyloxy group, 2-phenylpentyloxy group, 3-phenylpentyloxy group, 4-phenylpentyloxy group, 5-phenylpentyloxy group, 1-phenylhexyloxy group, 2-phenylhexyloxy group, 3-phenylhexyloxy group, 4-phenylhexyloxy group, 5-phenylhexyloxy group and 6-phenylhexyloxy group.

Examples of the heteroaryloxy groups which substitute the alkyl groups include heteroaryloxy groups having 2 to 14 carbon atoms and at least 1, preferably 1 to 3 heteroatoms such as nitrogen atoms, oxygen atoms and sulfur atoms. Specific examples thereof include 2-pyridyloxy group, 2-pyrazyloxy group, 2-pyrimidyloxy group and 2-quinolyloxy group.

The alkylthio groups which substitute the alkyl groups may be linear, branched or cyclic. Examples thereof include alkylthio groups having 1 to 6 carbon atoms. Specific examples include methylthio group, ethylthio group, n-propylthio group, isopropylthio group, n-butylthio group, 2-butylthio group, isobutylthio group, tert-butylthio group, pentylthio group, hexylthio group and cyclohexylthio group.

Examples of the arylthio groups which substitute the alkyl groups include arylthio groups having 6 to 14 carbon atoms. Specific examples include phenylthio group, tolylthio group, xylylthio group and naphthylthio group.

Examples of the aralkylthio groups which substitute the alkyl groups include aralkylthio groups having 7 to 12 carbon atoms. Specific examples include benzylthio group and 2-phenethylthio group.

Examples of the heteroarylthio groups which substitute the alkyl groups include heteroarylthio groups having 2 to 14 carbon atoms and at least 1, preferably 1 to 3 heteroatoms such as nitrogen atoms, oxygen atoms and sulfur atoms. Specific examples thereof include 4-pyridylthio group, 2-benzimidazolylthio group, 2-benzoxazolylthio group and 2-benzothiazolylthio group.

Examples of the substituted amino groups which substitute the alkyl groups include amino groups in which one or two hydrogen atoms of the amino group have been substituted with substituents such as alkyl groups, aryl groups or aralkyl groups. Specific examples of the amino groups substituted with alkyl groups, namely the alkyl group-substituted amino groups include mono- or dialkylamino groups such as N-methylamino group, N,N-dimethylamino group, N,N-diethylamino group, N,N-diisopropylamino group and N-cyclohexylamino group.

Specific examples of the amino groups substituted with aryl groups, namely the aryl group-substituted amino groups include mono- or diarylamino groups such as N-phenylamino group, N,N-diphenylamino group, N,N-ditolylamino group, N-naphthylamino group and N-naphthyl-N-phenylamino group. Specific examples of the amino groups substituted with aralkyl groups, namely the aralkyl group-substituted amino groups include mono- or diaralkylamino groups such as N-benzylamino group and N,N-dibenzylamino group.

Examples of the tri-substituted silyl groups which substitute the alkyl groups include trimethylsilyl group, triethylsilyl group, triisopropylsilyl group, tert-butyldimethylsilyl group, tert-butyldiphenylsilyl group and triphenylsilyl group.

Examples of the halogen atoms which substitute the alkyl groups include fluorine atom, chlorine atom, bromine atom and iodine atom. Exemplary halogenated alkyl groups include monofluoromethyl group, difluoromethyl group, trifluoromethyl group and pentafluoroethyl group.

Of these substituents, the hydrocarbon groups, the aliphatic heterocyclic groups, the aromatic heterocyclic groups, the alkoxy groups, the alkylenedioxy groups, the aryloxy groups, the aralkyloxy groups, the heteroaryloxy groups, the alkylthio groups, the arylthio groups, the aralkylthio groups, the heteroarylthio groups or the substituted amino groups may be further substituted with a group selected from the aforementioned substituents.

<Alkenyl Groups>

Examples of the alkenyl groups represented by $R^1$ to $R^{14}$ include linear, optionally branched chain or cyclic alkenyl groups having 2 to 15 carbon atoms, preferably 2 to 10 carbon atoms, and more preferably 2 to 6 carbon atoms. Specific examples include vinyl group, 1-propenyl group, 2-propenyl group, 1-butenyl group, 2-butenyl group, 3-butenyl group, 1-pentenyl group, 2-pentenyl group, 3-pentenyl group, 4-pentenyl group, 1-cyclopentenyl group, 3-cyclopentenyl group, 1-hexenyl group, 2-hexenyl group, 3-hexenyl group, 4-hexenyl group, 5-hexenyl group, 1-cyclohexenyl group and 3-cyclohexenyl group.

Further, these alkenyl groups may have a substituent. Examples of the substituents include alkyl groups, aryl groups, heterocyclic groups (aliphatic heterocyclic groups, aromatic heterocyclic groups) and halogen atoms. Specific examples thereof include those described above as the substituents for the alkyl groups.

<Alkynyl Groups>

Examples of the alkynyl groups represented by $R^1$ to $R^{14}$ include linear or optionally branched alkynyl groups having 2 to 15 carbon atoms, preferably 2 to 10 carbon atoms, and more preferably 2 to 6 carbon atoms. Specific examples include ethynyl group, 1-propynyl group, 2-propynyl group, 1-butynyl group, 2-butynyl group, 3-butynyl group, 1-pentynyl group, 2-pentynyl group, 3-pentynyl group, 4-pentynyl group, 1-hexynyl group, 2-hexynyl group, 3-hexynyl group, 4-hexynyl group and 5-hexynyl group.

Further, these alkynyl groups may have a substituent. Examples of the substituents include alkyl groups, aryl groups, heterocyclic groups (aliphatic heterocyclic groups, aromatic heterocyclic groups) and tri-substituted silyl groups. Specific examples thereof include those described above as the substituents for the alkyl groups.

<Aryl Groups>

Specific examples of the aryl groups represented by $R^1$ to $R^{14}$ include those aryl groups which are described above as the aryl groups which substitute the alkyl groups.

Further, these aryl groups may have a substituent. Examples of the substituents include alkyl groups, aryl groups, heterocyclic groups (aliphatic heterocyclic groups, aromatic heterocyclic groups) and halogen atoms. Specific examples thereof include those described above as the substituents for the alkyl groups.

{Optionally Substituted Heterocyclic Groups}

Examples of the optionally substituted heterocyclic groups represented by $R^1$ to $R^{14}$ include aliphatic or aromatic heterocyclic groups. Specific examples include the heterocyclic groups described above as the substituents for the alkyl groups. Further, these heterocyclic groups may have a substituent. Examples of the substituents include alkyl groups, aryl groups and heterocyclic groups. Specific examples thereof include those described above as the substituents for the alkyl groups.

{Optionally Substituted Alkoxy Groups}

Examples of the optionally substituted alkoxy groups represented by $R^1$ to $R^{14}$ include alkoxy groups and substituted alkoxy groups. The alkoxy groups may be linear, branched or cyclic. Examples thereof include alkoxy groups having 1 to 20 carbon atoms. Specific examples include methoxy group, ethoxy group, n-propoxy group, isopropoxy group, n-butoxy group, 2-butoxy group, isobutoxy group, tert-butoxy group, n-pentyloxy group, 2-methylbutoxy group, 3-methylbutoxy group, 2,2-dimethylpropyloxy group, n-hexyloxy group, 2-methylpentyloxy group, 3-methylpentyloxy group, 4-methylpentyloxy group, 5-methylpentyloxy group, heptyloxy group, octyloxy group, nonyloxy group, decyloxy group, cyclohexyloxy group, methoxymethoxy group and benzyloxy group. Of the alkoxy groups, alkoxy groups having 1 to 10 carbon atoms are preferable.

Further, these alkoxy groups may have a substituent. Examples of the substituents include alkyl groups, aryl groups, heterocyclic groups (aliphatic heterocyclic groups, aromatic heterocyclic groups) and halogen atoms. Specific examples thereof include those described above as the substituents for the alkyl groups.

{Optionally Substituted Aryloxy Groups}

Examples of the optionally substituted aryloxy groups represented by $R^1$ to $R^{14}$ include aryloxy groups and substituted aryloxy groups. Examples of the aryloxy groups include aryloxy groups having 6 to 20 carbon atoms. Specific examples thereof include phenoxy group, naphthoxy group and anthryloxy group. Of the aryloxy groups, aryloxy groups having 6 to 14 carbon atoms are preferable.

Further, these aryloxy groups may have a substituent. Examples of the substituents include alkyl groups, aryl groups, heterocyclic groups (aliphatic heterocyclic groups, aromatic heterocyclic groups) and halogen atoms. Specific examples thereof include those described above as the substituents for the alkyl groups.

{Optionally Substituted Acyl Groups}

The acyl groups represented by $R^1$ to $R^{14}$ may be linear, branched or cyclic. Examples thereof include acyl groups of 1 to 20 carbon atoms derived from acids such as carboxylic acids, sulfonic acids, sulfinic acids, phosphinic acids and phosphonic acid. Examples of the carboxylic acid-derived acyl groups include acyl groups derived from carboxylic acids such as aliphatic carboxylic acids and aromatic carboxylic acids. Specific examples of the carboxylic acid-derived acyl groups include formyl group, acetyl group, propionyl group, butyryl group, pivaloyl group, pentanoyl group, hexanoyl group, lauroyl group, stearoyl group, benzoyl group, 1-naphthoyl group, 2-naphthoyl group and trifluoroacetyl group. Of the acyl groups, acyl groups having 2 to 18 carbon atoms are preferable.

Examples of the sulfonic acid-derived acyl groups include alkylsulfonyl groups such as methanesulfonyl group, halogenated alkylsulfonyl groups such as trifluoromethanesulfonyl group, and arylsulfonyl groups such as benzenesulfonyl group and p-toluenesulfonyl group.

Examples of the sulfinic acid-derived acyl groups include alkylsulfinyl groups such as methanesulfinyl group, and arylsulfinyl groups such as benzenesulfinyl group.

Examples of the phosphonic acid-derived acyl groups include dialkylphosphinyl groups such as dimethylphosphinyl group, and diarylphosphinyl groups such as diphenylphosphinyl group.

Examples of the phosphonyl acid-derived acyl groups include dialkylphosphonyl groups such as dimethylphosphonyl group, and diarylphosphoryl groups such as diphenylphosphonyl group.

Further, these acyl groups may have a substituent. That is, a substituent may be introduced into at least one position of the acyl group. Examples of the substituents include hydrocarbon groups and heterocyclic groups (aliphatic heterocyclic groups, aromatic heterocyclic groups). Specific examples thereof include those described above as the substituents for the alkyl groups.

{Optionally Substituted Alkoxycarbonyl Groups}

Examples of the optionally substituted alkoxycarbonyl groups represented by $R^1$ to $R^{14}$ include alkoxycarbonyl groups and substituted alkoxycarbonyl groups. The alkoxycarbonyl groups may be linear, branched or cyclic. Examples thereof include alkoxycarbonyl groups having 2 to 20 carbon atoms. Specific examples thereof include methoxycarbonyl group, ethoxycarbonyl group, n-propoxycarbonyl group, isopropoxycarbonyl group, n-butoxycarbonyl group, tert-butoxycarbonyl group, pentyloxycarbonyl group, hexyloxycarbonyl group, 2-ethylhexyloxycarbonyl group, lauryloxycarbonyl group, stearyloxycarbonyl group and cyclohexyloxycarbonyl group.

Further, these alkoxycarbonyl groups may have a substituent. Examples of the substituents include alkyl groups, aryl groups, halogen atoms, heterocyclic groups (aliphatic heterocyclic groups, aromatic heterocyclic groups) and alkoxy groups. Specific examples thereof include those described above as the substituents for the alkyl groups.

{Optionally Substituted Aryloxycarbonyl Groups}

Examples of the optionally substituted aryloxycarbonyl groups represented by $R^1$ to $R^{14}$ include aryloxycarbonyl groups and substituted aryloxycarbonyl groups. Examples of the aryloxycarbonyl groups include aryloxycarbonyl groups having 7 to 20 carbon atoms. Specific examples thereof include phenoxycarbonyl group and naphthyloxycarbonyl group.

Further, these aryloxycarbonyl groups may have a substituent on the aryl group. Examples of the substituents include alkyl groups, aryl groups, alkoxy groups and halogen atoms. Specific examples thereof include those described above as the substituents for the alkyl groups.

{Optionally Substituted Carbamoyl Groups}

Examples of the optionally substituted carbamoyl groups represented by $R^1$ to $R^{14}$ include carbamoyl group and substituted carbamoyl groups. Examples of the substituted carbamoyl groups include carbamoyl groups in which one or two hydrogen atoms of the amino group in the carbamoyl group have been substituted with substituents such as optionally substituted hydrocarbon groups. The optionally substituted hydrocarbon groups may be similar to the optionally substituted hydrocarbon groups described above as the substituents for the alkyl groups. Specific examples of the substituted carbamoyl groups include N-methylcarbamoyl group, N,N-diethylcarbamoyl group and N-phenylcarbamoyl group.

{Optionally Substituted Alkylthiocarbonyl Groups}

Examples of the optionally substituted alkylthiocarbonyl groups represented by $R^1$ to $R^{14}$ include alkylthiocarbonyl groups and substituted alkylthiocarbonyl groups. The alkylthiocarbonyl groups may be linear, branched or cyclic. Examples thereof include alkylthiocarbonyl groups having 2 to 20 carbon atoms. Specific examples thereof include methylthiocarbonyl group, ethylthiocarbonyl group, n-propylthiocarbonyl group, isopropylthiocarbonyl group, n-butylthiocarbonyl group, tert-butylthiocarbonyl group, pentylthiocarbonyl group, hexylthiocarbonyl group, 2-ethylhexylthiocarbonyl group, laurylthiocarbonyl group, stearylthiocarbonyl group and cyclohexylthiocarbonyl group.

Further, these alkylthiocarbonyl groups may have a substituent. Examples of the substituents include alkyl groups, aryl groups, halogen atoms, heterocyclic groups (aliphatic heterocyclic groups, aromatic heterocyclic groups) and halogen atoms. Specific examples thereof include those described above as the substituents for the alkyl groups.

{Optionally Substituted Arylthiocarbonyl Groups}

Examples of the optionally substituted arylthiocarbonyl groups represented by $R^1$ to $R^{14}$ include arylthiocarbonyl groups and substituted arylthiocarbonyl groups. Examples of the arylthiocarbonyl groups include arylthiocarbonyl groups having 7 to 20 carbon atoms. Specific examples thereof include phenylthiocarbonyl group and naphthylthiocarbonyl group.

Further, these arylthiocarbonyl groups may have a substituent. Examples of the substituents include alkyl groups, aryl groups, halogen atoms, heterocyclic groups (aliphatic heterocyclic groups, aromatic heterocyclic groups) and halogen atoms. Specific examples thereof include those described above as the substituents for the alkyl groups.

{Optionally Substituted Alkylthio Groups}

Examples of the optionally substituted alkylthio groups represented by $R^1$ to $R^{14}$ include alkylthio groups and substituted alkylthio groups. The alkylthio groups may be linear, branched or cyclic. Examples thereof include alkylthio groups having 1 to 20 carbon atoms. Specific examples thereof include methylthio group, ethylthio group, n-propylthio group, isopropylthio group, n-butylthio group, 2-butylthio group, isobutylthio group, tert-butylthio group, pentylthio group, hexylthio group and cyclohexylthio group. Of the alkylthio groups, alkylthio groups having 1 to 10 carbon atoms are preferable, and alkylthio groups having 1 to 6 carbon atoms are more preferable.

Further, these alkylthio groups may have a substituent. Examples of the substituents include alkyl groups, aryl groups, halogen atoms, heterocyclic groups (aliphatic heterocyclic groups, aromatic heterocyclic groups) and halogen atoms. Specific examples thereof include those described above as the substituents for the alkyl groups.

{Optionally Substituted Arylthio Groups}

Examples of the optionally substituted arylthio groups represented by $R^1$ to $R^{14}$ include arylthio groups and substituted arylthio groups. Examples of the arylthio groups include arylthio groups having 6 to 20 carbon atoms. Specific examples thereof include phenylthio group and naphthylthio group. Of the arylthio groups, arylthio groups having 6 to 14 carbon atoms are preferable.

Further, these arylthio groups may have a substituent. Examples of the substituents include alkyl groups, aryl groups, halogen atoms, heterocyclic groups (aliphatic heterocyclic groups, aromatic heterocyclic groups) and halogen atoms. Specific examples thereof include those described above as the substituents for the alkyl groups.

{Optionally Substituted Amino Groups}

Examples of the optionally substituted amino groups represented by $R^1$ to $R^{14}$ include amino group and substituted amino groups. Examples of the substituted amino groups include amino groups in which one or two hydrogen atoms of the amino group have been substituted with substituents such as protective groups. The protective groups may be any groups used as amino protective groups. Examples include those described as amino protective groups in "PROTECTIVE GROUPS IN ORGANIC SYNTHESIS THIRD EDITION (JOHN WILEY & SONS, INC. (1999)". Specific examples of the amino protective groups include optionally substituted hydrocarbon groups (such as alkyl groups, aryl groups and aralkyl groups), acyl groups, optionally substituted alkoxycarbonyl groups, optionally substituted aryloxycarbonyl groups and optionally substituted aralkyloxycarbonyl groups. The optionally substituted hydrocarbon groups, the acyl groups, the optionally substituted alkoxycarbonyl groups, the optionally substituted aryloxycarbonyl groups and the optionally substituted aralkyloxycarbonyl groups may be similar to those groups described with respect to the above protective groups.

Specific examples of the amino groups substituted with alkyl groups, namely the alkyl group-substituted amino groups include mono- or dialkylamino groups such as N-methylamino group, N,N-dimethylamino group, N,N-diethylamino group, N,N-diisopropylamino group, N-methyl-N-isopropylamino group and N-cyclohexylamino group.

Specific examples of the amino groups substituted with aryl groups, namely the aryl group-substituted amino groups include mono- or diarylamino groups such as N-phenylamino group, N,N-diphenylamino group, N-naphthylamino group and N-naphthyl-N-phenylamino group.

Specific examples of the amino groups substituted with aralkyl groups, namely the aralkyl group-substituted amino groups include mono- or diaralkylamino groups such as N-benzylamino group and N,N-dibenzylamino group. Examples further include di-substituted amino groups such as N-methyl-N-phenylamino group and N-benzyl-N-methylamino group.

Specific examples of the amino groups substituted with acyl groups, namely the acylamino groups include formylamino group, acetylamino group, propionylamino group, pivaloylamino group, pentanoylamino group, hexanoylamino group, benzoylamino group, $-NHSO_2CH_3$, $-NHSO_2C_6H_5$, $-NHSO_2C_6H_4CH_3$, $-NHSO_2CF_3$ and $-NHSO_2N(CH_3)_2$.

Specific examples of the amino groups substituted with alkoxycarbonyl groups, namely the alkoxycarbonylamino groups include methoxycarbonylamino group, ethoxycarbonylamino group, n-propoxycarbonylamino group, n-butoxycarbonylamino group, tert-butoxycarbonylamino group, pentyloxycarbonylamino group and hexyloxycarbonylamino group.

Specific examples of the amino groups substituted with aryloxycarbonyl groups, namely the aryloxycarbonylamino groups include amino groups in which one hydrogen atom of the amino group has been substituted with any of the aforementioned aryloxycarbonyl groups. Specific examples thereof include phenoxycarbonylamino group and naphthyloxycarbonylamino group.

Specific examples of the amino groups substituted with aralkyloxycarbonyl groups, namely the aralkyloxycarbonylamino groups include benzyloxycarbonylamino group.

{Substituted Silyl Groups}

Examples of the substituted silyl groups represented by $R^1$ to $R^{14}$ include tri-substituted silyl groups in which three hydrogen atoms of the silyl group have been substituted with substituents such as alkyl groups, substituted alkyl groups, aryl groups, substituted aryl groups, aralkyl groups, substituted aralkyl groups, alkoxy groups and substituted alkoxy groups. The alkyl groups, the substituted alkyl groups, the aryl groups, the substituted aryl groups, the aralkyl groups, the substituted aralkyl groups, the alkoxy groups and the substituted alkoxy groups may be similar to those groups described above as the substituents for the alkyl groups.

Specific examples of the substituted silyl groups include trimethylsilyl group, triethylsilyl group, triisopropylsilyl group, tert-butyldimethylsilyl group, tert-butyldiphenylsilyl group, triphenylsilyl group, tert-butylmethoxyphenylsilyl group and tert-butoxydiphenylsilyl group.

{Halogen Atoms}

Examples of the halogen atoms represented by $R^1$ to $R^{14}$ include fluorine atom, chlorine atom, bromine atom and iodine atom.

{Ring Formation}

Referring to General Formula (1), in any combination of $R^1$ to $R^{14}$, these substituents may be linked together to form a ring. Examples of possibly formed rings include six-membered rings as well as six-membered rings or five-membered rings having a six-membered ring, which are condensed to the aryl rings a to d in General Formula (1A) (General Formula (1A) is identical to General Formula (1) except that the aryl rings in General Formula (1) have been assigned with reference sings a to d).

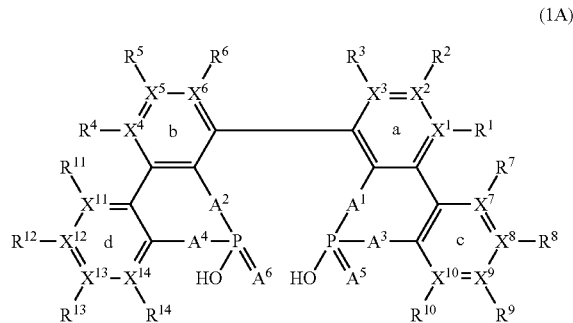

(1A)

{Preferred Examples of $R^1$ to $R^{14}$}

$R^1$, $R^4$, $R^7$ and $R^{11}$ are preferably each independently a hydrogen atom or a linear, branched or cyclic alkyl group having 1 to 6 carbon atoms; in detail, hydrogen atom, methyl group, ethyl group, n-propyl group, isopropyl group, n-butyl group, sec-butyl group, isobutyl group and tert-butyl group are preferable, and hydrogen atom is particularly preferable.

$R^8$, $R^9$, $R^{12}$ and $R^{13}$ are preferably each independently a hydrogen atom, a halogen atom, an optionally substituted, linear, branched or cyclic alkyl group having 1 to 6 carbon atoms, an optionally substituted, linear, branched or cyclic alkoxy group having 1 to 10 carbon atoms, or an optionally substituted aryl group having 6 to 20 carbon atoms. In detail, hydrogen atom, halogen atom, methyl group, ethyl group, n-propyl group, isopropyl group, n-butyl group, sec-butyl group, isobutyl group, tert-butyl group, methoxy group, ethoxy group, n-propoxy group, isopropoxy group, n-butoxy group, 2-butoxy group, isobutoxy group, tert-butoxy group, phenyl group, 1-naphthyl group, 2-naphthyl group and anthryl group are particularly preferable.

It is preferable that $R^2$, $R^3$, $R^5$ and $R^6$ be groups other than hydrogen atoms. Further, it is preferable that $R^2$ and $R^3$ be linked together to form a six-membered ring, further preferably a six-membered ring or a five-membered ring having a six-membered ring, which is condensed to the ring a. It is particularly preferable that $R^2$ and $R^3$ be linked together to form a six-membered ring which is condensed to the ring a, thus forming a naphthyl skeleton in combination with the ring a.

It is preferable that $R^5$ and $R^6$ be linked together to form a six-membered ring, further preferably a six-membered ring or a five-membered ring having a six-membered ring, which is condensed to the ring b. It is particularly preferable that $R^5$ and $R^6$ be linked together to form a six-membered ring which is condensed to the ring b, thus forming a naphthyl skeleton in combination with the ring b.

$R^{10}$ and $R^{14}$ are preferably each independently a hydrogen atom, a halogen atom, an optionally substituted, linear, branched or cyclic alkyl group having 1 to 6 carbon atoms, an optionally substituted, linear, branched or cyclic alkoxy group having 1 to 10 carbon atoms, or an optionally substituted aryl group having 6 to 20 carbon atoms. In detail, hydrogen atom, halogen atom, methyl group, ethyl group, n-propyl group, isopropyl group, n-butyl group, sec-butyl group, isobutyl group, tert-butyl group, methoxy group, ethoxy group, n-propoxy group, isopropoxy group, n-butoxy group, 2-butoxy group, isobutoxy group, tert-butoxy group, optionally substituted phenyl group, optionally substituted 1-naphthyl group, optionally substituted 2-naphthyl group and optionally substituted anthryl group are preferable, and optionally substituted phenyl group is particularly preferable.

When groups $R^8$ to $R^{10}$ and $R^{12}$ to $R^{14}$ have substituents, the substituents are particularly preferably linear or branched alkyl groups having 1 to 6 carbon atoms.

$R^8$ and $R^9$ may be linked together to form a six-membered ring, or a six-membered ring or a five-membered ring having a six-membered ring, which is condensed to the ring c. In detail, $R^8$ and $R^9$ may be linked together to form a six-membered ring which is condensed to the ring c, thus forming a naphthyl skeleton in combination with the ring c. $R^9$ and $R^{10}$ may be linked together to form a six-membered ring, or a six-membered ring or a five-membered ring having a six-membered ring, which is condensed to the ring c. In detail, $R^9$ and $R^{10}$ may be linked together to form a six-membered ring which is condensed to the ring c, thus forming a naphthyl skeleton in combination with the ring c. $R^{12}$ and $R^{13}$ may be linked together to form a six-membered ring, or a six-membered ring or a five-membered ring having a six-membered ring, which is condensed to the ring d. In detail, $R^{12}$ and $R^{13}$ may be linked together to form a six-membered ring which is condensed to the ring d, thus forming a naphthyl skeleton in combination with the ring c. $R^{13}$ and $R^{14}$ may be linked together to form a six-membered ring, or a six-membered ring or a five-membered ring having a six-membered ring, which is condensed to the ring d. In detail, $R^{13}$ and $R^{14}$ may be linked together to form a six-membered ring which is condensed to the ring d, thus forming a naphthyl skeleton in combination with the ring c.

[2] $X^1$ to $X^{14}$

In General Formula (1), $X^1$ to $X^{14}$ each independently represent a carbon atom or a nitrogen atom. In the case of a nitrogen atom, there is no substituent on the nitrogen atom. Preferably, $X^1$ to $X^{14}$ are carbon atoms.

[3] $A^1$ to $A^6$

In General Formula (1), $A^1$ to $A^6$ each independently represent an oxygen atom or a sulfur atom. Preferably, $A^1$ to $A^6$ are oxygen atoms.

[4] Tetraaryl Skeleton

The bis-phosphate compound represented by General Formula (1) has a tetraaryl skeleton. Examples of the tetraaryl skeletons include groups which can have an axially chiral structure such as 3,3'-aryl-1,1'-biphenyldiyl group, 3,3'-aryl-1,1'-binaphthalenediyl group, 3,3'-aryl-1,1'-phenylpyridyl group and 3,3'-aryl-1,1'-bipyridyl group. These groups may be optically active or inactive, but are preferably optically active.

Specific examples of the tetraaryl skeletons of the bis-phosphate compounds according to the invention include the following structures. However, the tetraaryl skeletons are not limited thereto. (The following structural formulae illustrate inventive bis-phosphate compounds of General Formula (1) while omitting the phosphate moieties. In the following, "Me" represents methyl group, "Et" ethyl group, "t-Bu" tert-butyl group, "i-Pr" isopropyl group and "Ph" phenyl group. In the following, the rings a to d correspond to the respective rings a to d in General Formula (1A).)

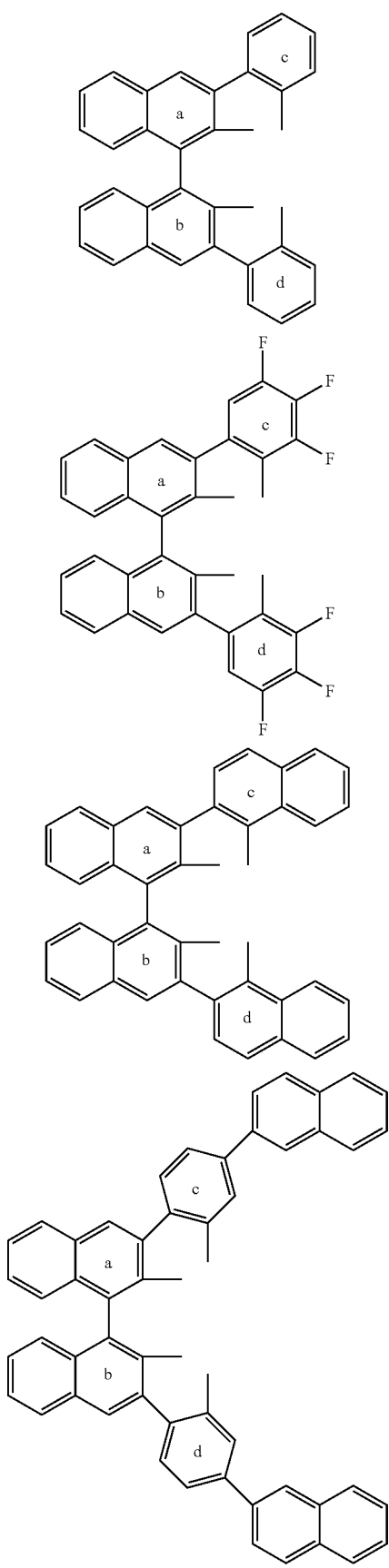
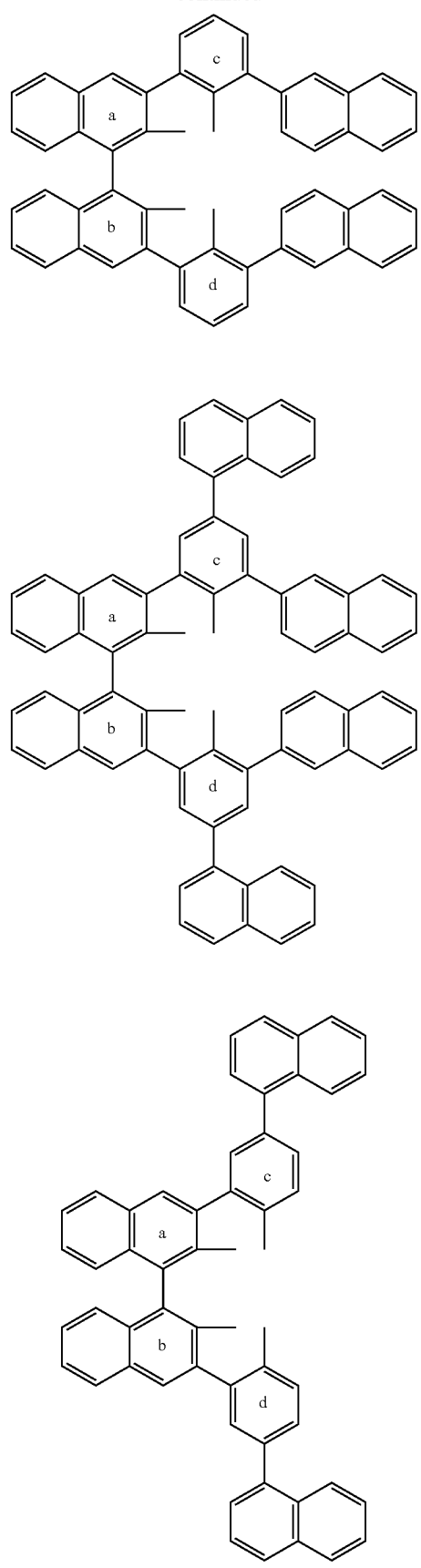

-continued
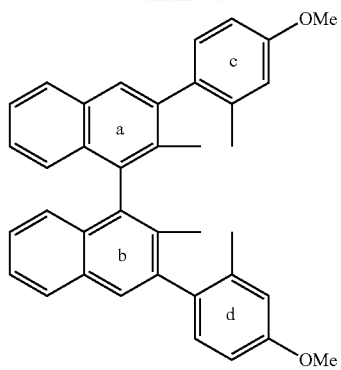
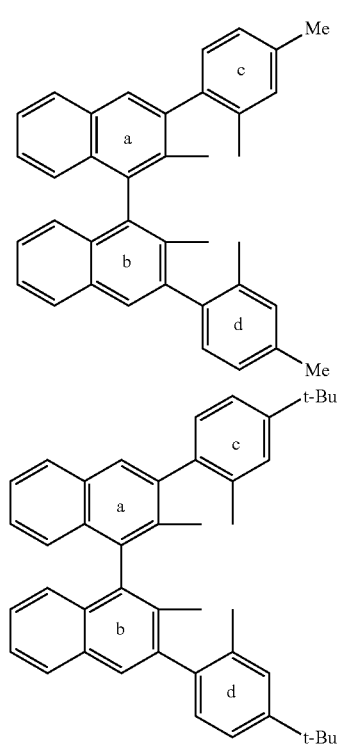
-continued
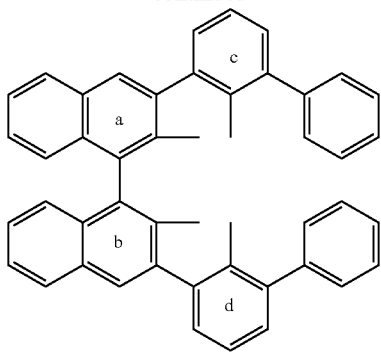
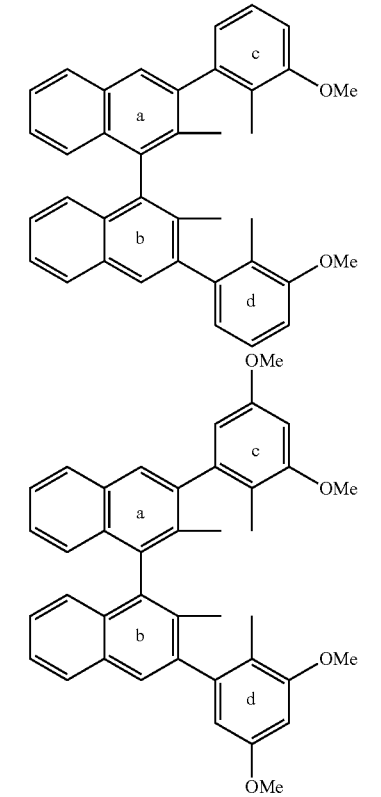

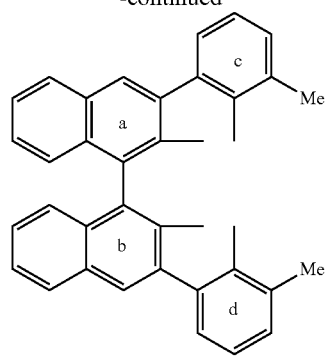
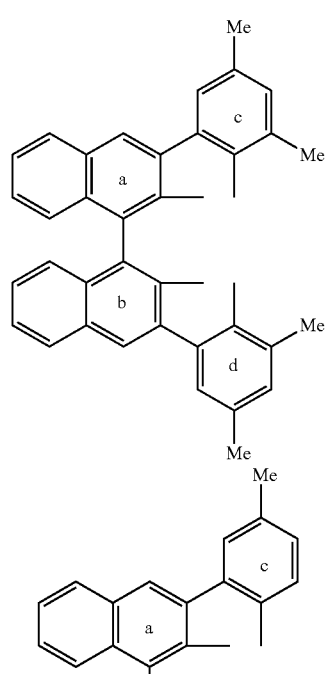
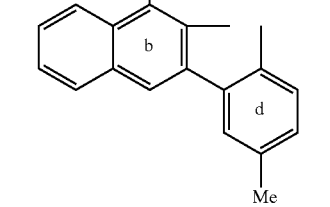
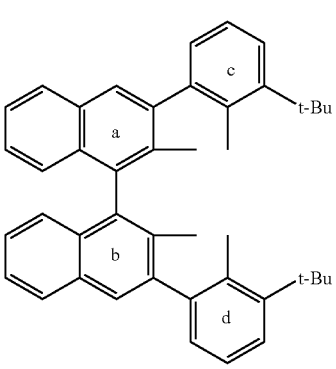
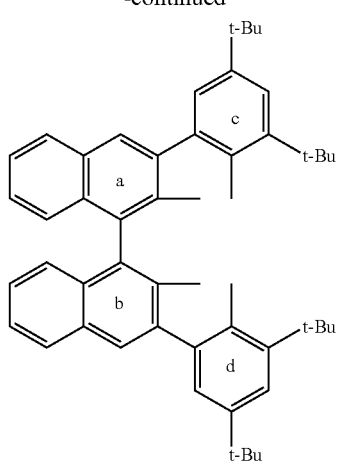
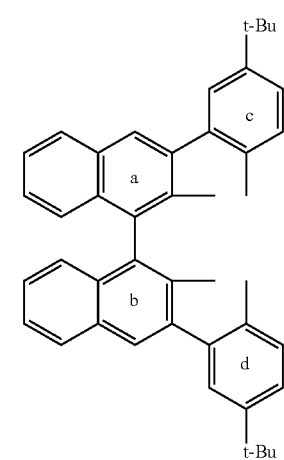
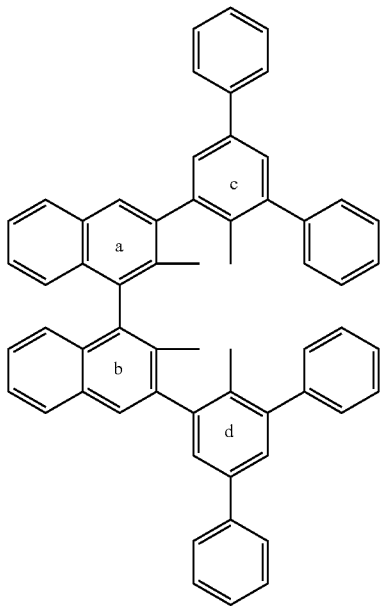

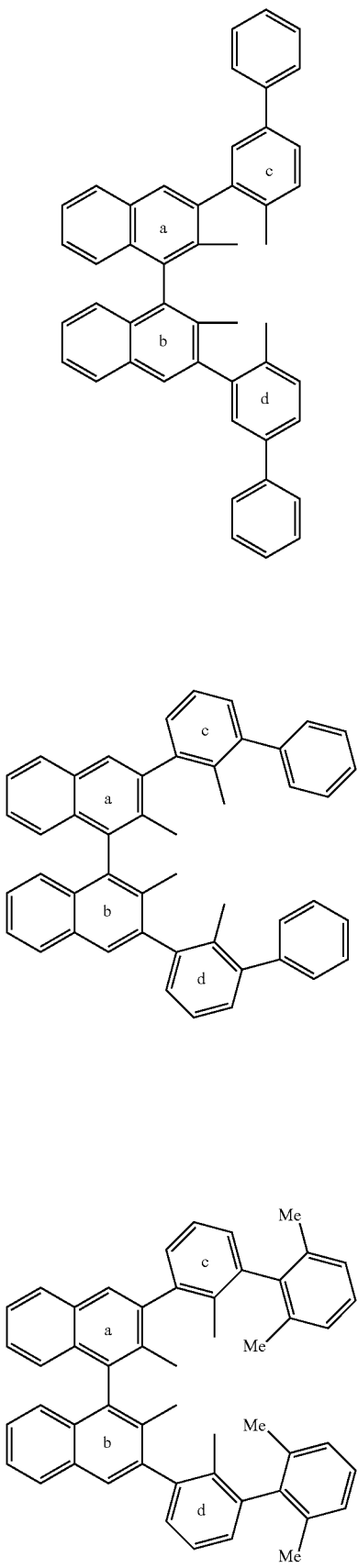

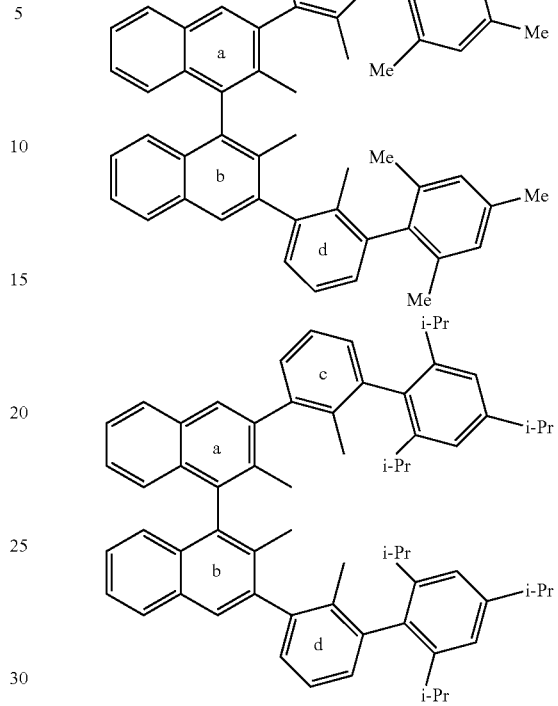

The following skeletons are particularly preferable as the tetraaryl skeletons of the inventive bis-phosphate compounds.

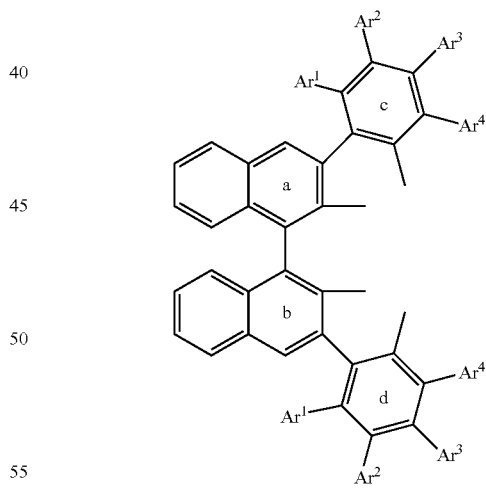

In the above formula, $Ar^1$ to $Ar^4$ each represent the corresponding substituent among $R^7$ to $R^{10}$ and $R^{11}$ to $R^{14}$, and are each preferably a hydrogen atom or an optionally substituted aryl group, and particularly preferably an optionally substituted phenyl group, an optionally substituted anthryl group or an optionally substituted naphthyl group.

Further, it is preferable that the tetraaryl skeletons of the inventive bis-phosphate compounds have an optically active site in the structure as illustrated in General Formulae (I-1) and (1-2) below.

(1-1)
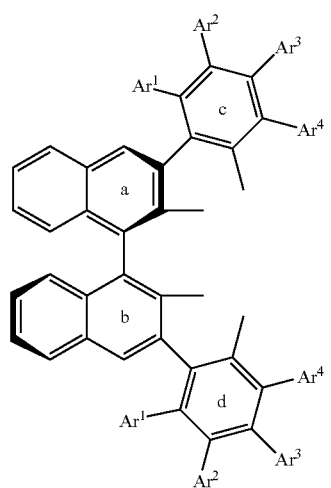
(1-2)
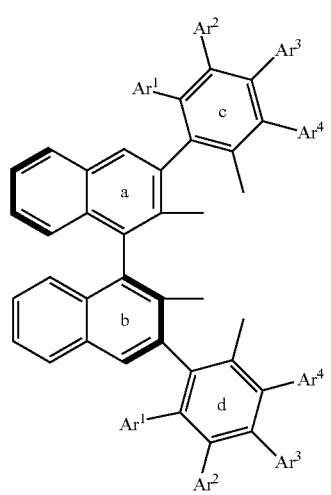
Of these optically active tetraaryl skeletons, those having the following structures are particularly preferable.
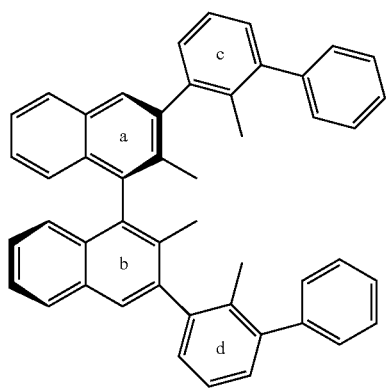
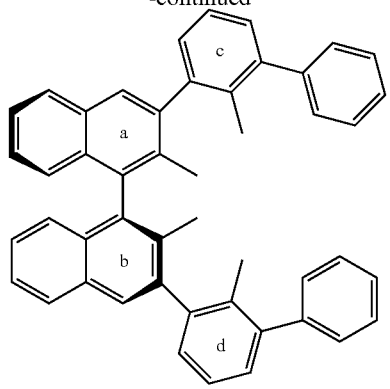
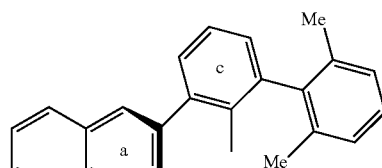
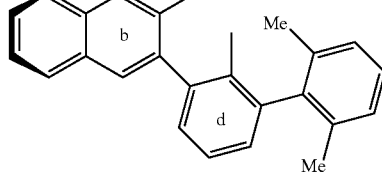
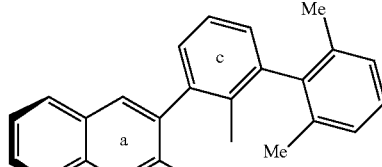
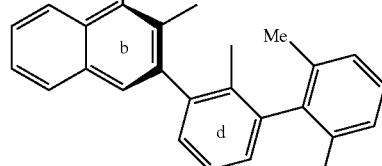
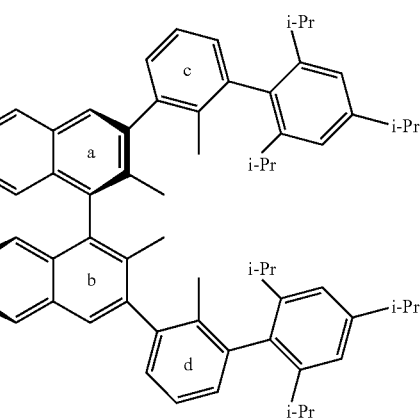

-continued

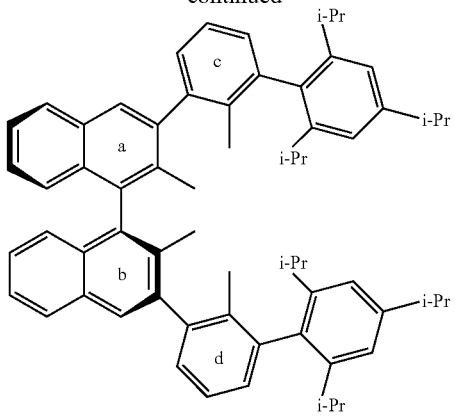

[5] Preferable Specific Examples

In particular, the following compounds are preferable as the inventive bis-phosphate compounds represented by General Formula (1).

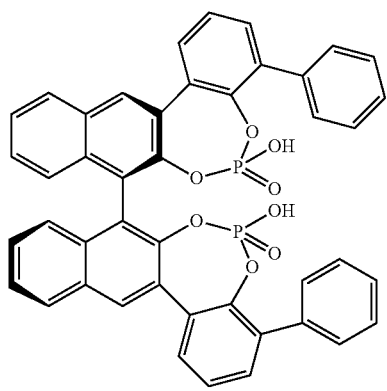

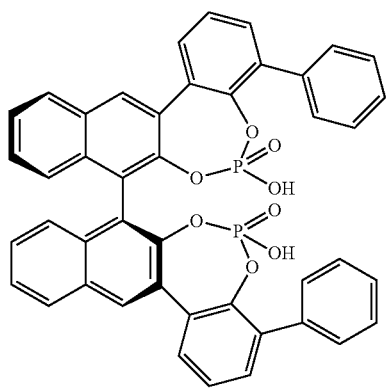

-continued

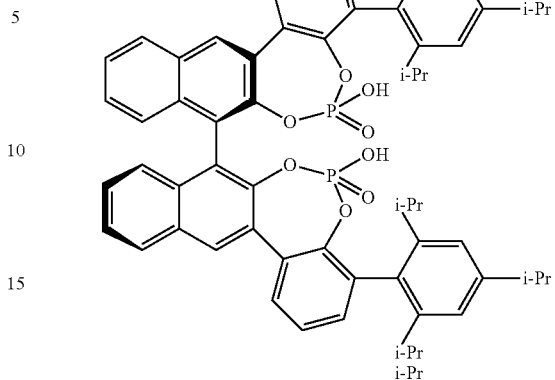

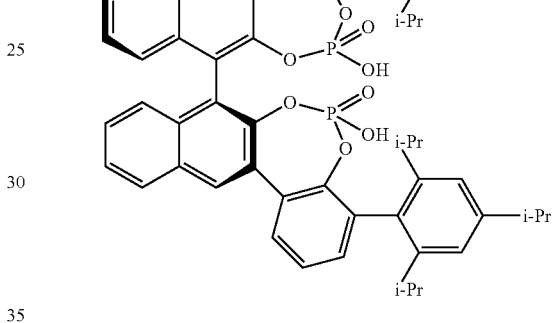

[6] Metal Salts or Ammonium Salt

In the inventive bis-phosphate compound represented by General Formula (1), the —OH group in the phosphate moiety may form a metal salt, an ammonium salt or an amine salt.

Examples of the metal salts include salts of alkali metals such as lithium, sodium, potassium, rubidium and cesium, salts of alkaline earth metals such as magnesium, calcium, strontium and barium, and salts of transition metals such as titanium, manganese, iron, copper, tin, zinc, cobalt and nickel.

The ammonium salt is a salt with ammonia. Examples of the amine salts include salts with amines such as aliphatic amines such as methylamine, ethylamine, propylamine, butylamine, cyclohexylamine, dimethylamine, diethylamine, diisopropylamine, triethylamine, tripropylamine, diisopropylethylamine, di(2-ethylhexyl)amine, hexadecylamine, tri-n-butylamine and N-methylmorpholine, aromatic amines such as N,N-dimethylaniline, pyridine and 4-dimethylaminopyridine, and saturated heterocyclic amines such as piperidine.

[7] Production Method

For example, the inventive bis-phosphate compound represented by General Formula (1) may be produced in the following manner.

Specifically, the bis-phosphate compound represented by General Formula (1) may be obtained by reacting a compound represented by General Formula (N) below with a phosphorylating agent.

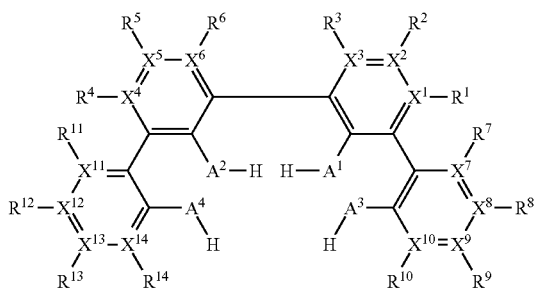

(N)

In the formula, $R^1$ to $R^{14}$, $X^1$ to $X^{14}$ and $A^1$ to $A^4$ are defined to be the same as those in General Formula (1).

Hereinafter, the compounds will be represented by General Formula (n) below in which the tetraaryl skeleton in General Formula (N) is abbreviated.

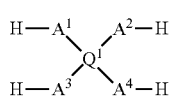

(n)

In the formula, $Q^1$ represents the tetraaryl skeleton according to the invention. $A^1$ to $A^4$ are defined to be the same as those in General Formula (1).

Examples of the compounds represented by General Formula (n) (hereinafter, sometimes abbreviated as "compounds (n)") include tetraols, mercapto triols, dimercapto diols, trimercapto alcohols and tetrathiols.

Examples of the tetraols include tetraols represented by General Formula (n-1) below.

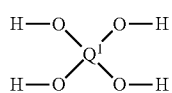

(n-1)

In the formula, $Q^1$ is defined to be the same as that in General Formula (n).

Specific examples of the tetraols include 1,1'-binaphthalene-3,3'-(2-hydroxyphenyl)-2,2'-diol, 5,5',6,6',7,7',8,8'-octahydro(1,1-binaphthalene)-3,3'-(2-hydroxyphenyl)-2,2'-diol, 1,1'-biphenyl-3,3'-(2-hydroxyphenyl)-2,2'-diol and 1,1'-binaphthalene-3,3'-(3-phenyl-2-hydroxyphenyl)-2,2'-diol.

Examples of the mercapto triols include mercapto triols represented by General Formula (n-2) below.

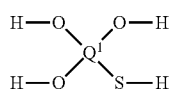

(n-2)

In the formula, $Q^1$ is defined to be the same as that in General Formula (n).

Specific examples of the mercapto triols include 1,1'-binaphthalene-3-(2-hydroxyphenyl)-3'-(2-thiolphenyl)-2,2'-diol, 1,1'-binaphthalene-3,3'-(2-hydroxyphenyl)-2-hydroxy-2'-thiol, 5,5',6,6',7,7',8,8'-octahydro(1,1-binaphthalene)-3-(2-hydroxyphenyl)-3'-(2-thiolphenyl)-2,2'-diol, 1,1'-biphenyl-3,3'-(2-hydroxyphenyl)-2-hydroxy-2'-thiol, 1,1'-binaphthalene-3-(2-hydroxyphenyl)-3'-(2-thiolphenyl)-2,2'-diol and 1,1'-binaphthalene-3,3'-(3-phenyl-2-hydroxyphenyl)-2-hydroxy-2'-thiol.

Examples of the dimercapto diols include dimercapto diols represented by General Formula (n-3) below.

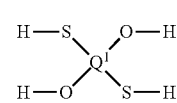

(n-3)

In the formula, $Q^1$ is defined to be the same as that in General Formula (n).

Specific examples of the dimercapto diols include 1,1'-binaphthalene-3-(2-hydroxyphenyl)-3'-(2-thiolphenyl)-2-hydroxy-2'-thiol, 1,1'-binaphthalene-3-(2-hydroxyphenyl)-3'-(2-thiolphenyl)-2'-hydroxy-2-thiol, 1,1'-binaphthalene-3,3'-(2-hydroxyphenyl)-2,2'-dithiol, 1,1'-binaphthalene-3,3'-(2-thiolphenyl)-2,2'-diol, 5,5',6,6',7,7',8,8'-octahydro(1,1-binaphthalene)-3-(2-hydroxyphenyl)-3'-(2-thiolphenyl)-2-hydroxy-2'-thiol, 5,5',6,6',7,7',8,8'-octahydro(1,1-binaphthalene)-3-(2-hydroxyphenyl)-3'-(2-thiolphenyl)-2'-hydroxy-2-thiol, 5,5',6,6',7,7',8,8'-octahydro(1,1-binaphthalene)-3,3'-(2-hydroxyphenyl)-2,2'-dithiol, 5,5',6,6',7,7',8,8'-octahydro(1,1-binaphthalene)-3,3'-(2-thiolphenyl)-2,2'-diol, 1,1'-biphenyl-3-(2-hydroxyphenyl)-3'-(2-thiolphenyl)-2-hydroxy-2'-thiol, 1,1'-biphenyl-3-(2-hydroxyphenyl)-3'-(2-thiolphenyl)-2'-hydroxy-2-thiol, 1,1'-biphenyl-3,3'-(2-hydroxyphenyl)-2,2'-dithiol, 1,1'-biphenyl-3,3'-(2-thiolphenyl)-2,2'-diol, 1,1'-binaphthalene-3,3'-(3-phenyl-2-hydroxyphenyl)-2,2'-dithiol, 1,1'-binaphthalene-3-(3-phenyl-2-hydroxyphenyl)-3'-(3-phenyl-2-thiolphenyl)-2-hydroxy-2'-thiol and 1,1'-binaphthalene-3,3'-(3-phenyl-2-thiolphenyl)-2,2'-diol.

Examples of the trimercapto alcohols include trimercapto alcohols represented by General Formula (n-4) below.

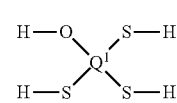

(n-4)

In the formula, $Q^1$ is defined to be the same as that in General Formula (n).

Specific examples of the trimercapto alcohols include 1,1'-binaphthalene-3-(2-hydroxyphenyl)-3'-(2-thiolphenyl)-2,2'-dithiol, 1,1'-binaphthalene-3,3'-(2-thiolphenyl)-2-hydroxy-2'-thiol, 5,5',6,6',7,7',8,8'-octahydro(1,1-binaphthalene)-3-(2-hydroxyphenyl)-3'-(2-thiolphenyl)-2,2'-dithiol, 1,1'-biphenyl-3,3'-(2-thiolphenyl)-2-hydroxy-2'-thiol, 1,1'-binaphthalene-3-(2-hydroxyphenyl)-3'-(2-thiolphenyl)-2,2'-dithiol and 1,1'-binaphthalene-3,3'-(3-phenyl-2-thiolphenyl)-2-hydroxy-2'-thiol.

Examples of the tetrathiols include tetrathiols represented by General Formula (n-5) below.

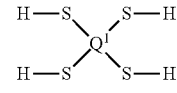

(n-5)

In the formula, $Q^1$ is defined to be the same as that in General Formula (n).

Specific examples of the tetrathiols include 1,1'-binaphthalene-3,3'-(2-thiolphenyl)-2,2'-dithiol, 5,5',6,6',7,7',8,8'-octahydro(1,1-binaphthalene)-3,3'-(2-thiolphenyl)-2,2'-dithiol, 1,1'-biphenyl-3,3'-(2-thiolphenyl)-2,2'-dithiol and 1,1'-binaphthalene-3,3'-(3-phenyl-2-thiolphenyl)-2,2'-dithiol.

In order to obtain an optically active bis-phosphate compound which has a tetraaryl skeleton represented by General Formula (1-1) or (1-2) as the bis-phosphate compound represented by General Formula (1), it is preferable to use an optically active compound represented by General Formula (na) below as the compound (n).

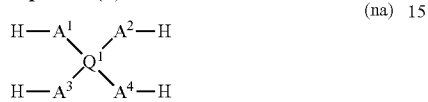
(na)

In the formula, $Q^{1*}$ represents a tetraaryl skeleton according to the invention which has an optically active site. $A^1$ to $A^4$ are defined to be the same as those in General Formula (1).

The same applies to the compounds represented by aforementioned General Formulae (n-1) to (n-5).

The optically active compounds represented by General Formula (na) may be any of compounds including those mentioned above as exemplary compounds (n) such as the tetraols, the mercapto triols, the dimercapto diols, the trimercapto alcohols and the tetrathiols as long as the compounds are optically active.

Specific examples of the optically active compounds represented by General Formula (na) which are tetraols as representative examples include the following compounds.

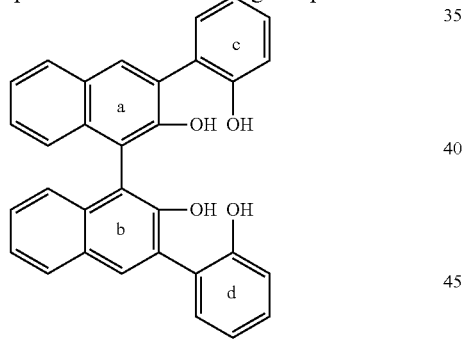

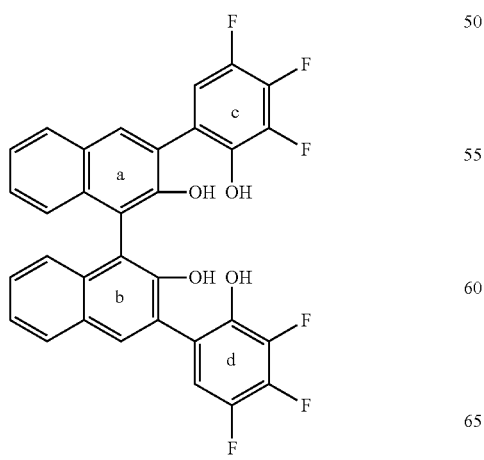

-continued

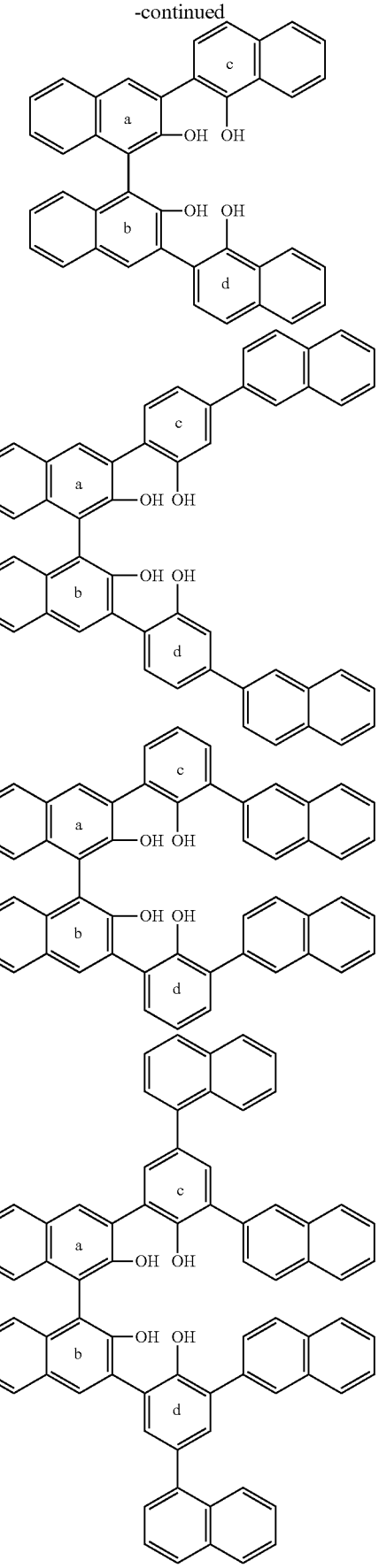

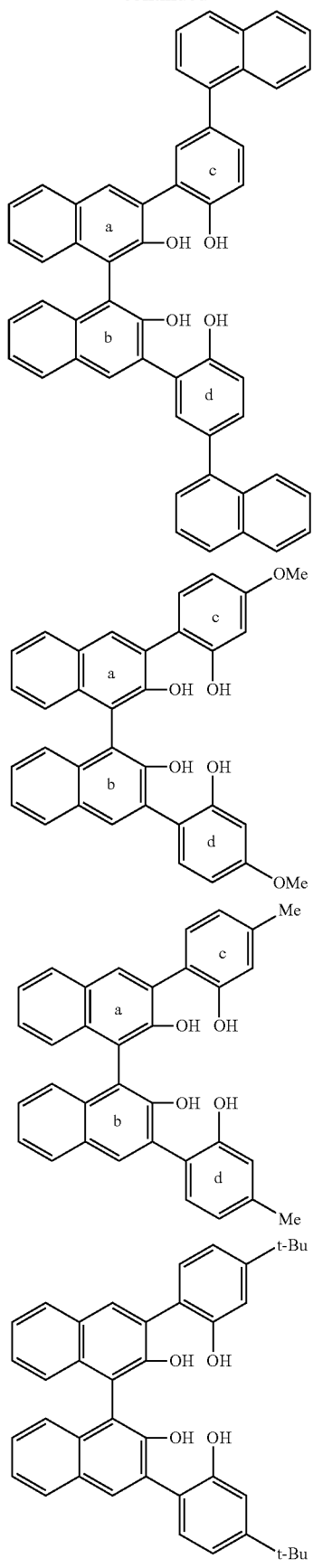
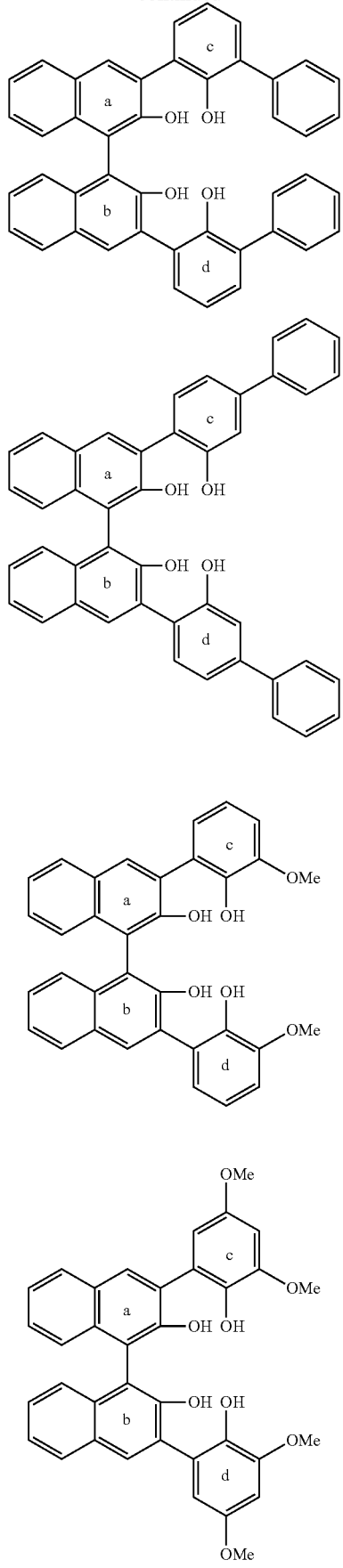

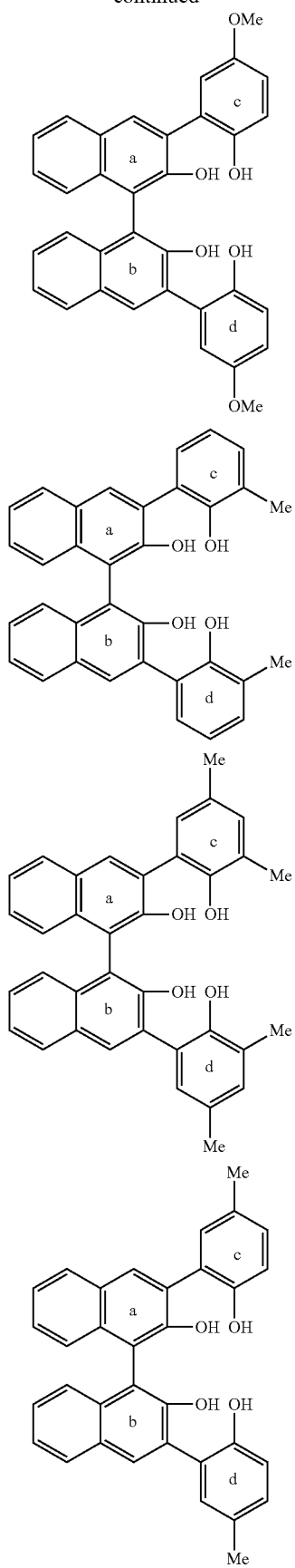
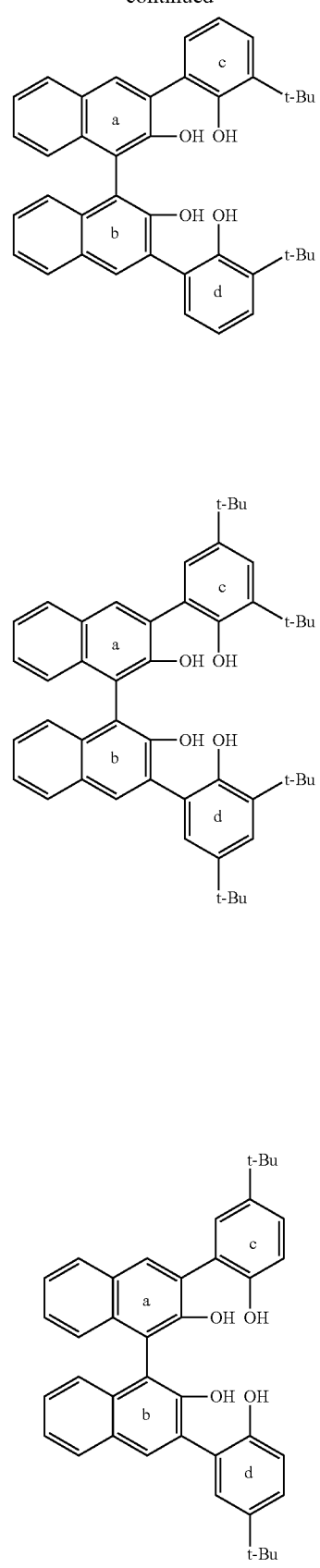

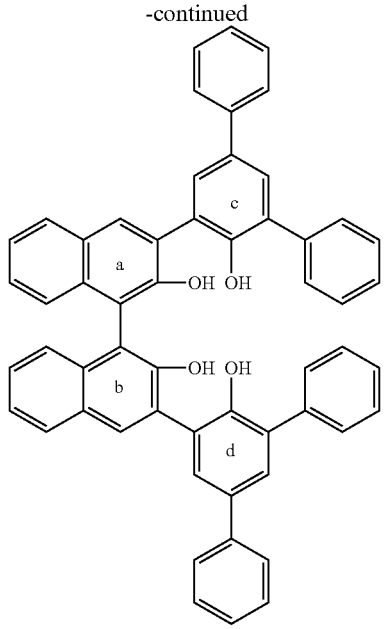
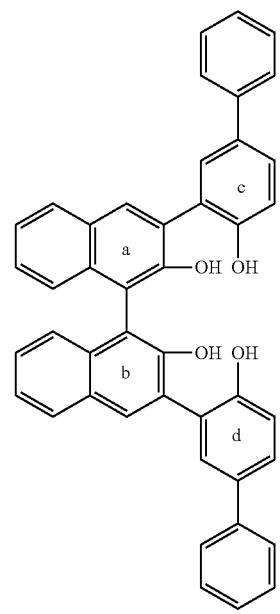
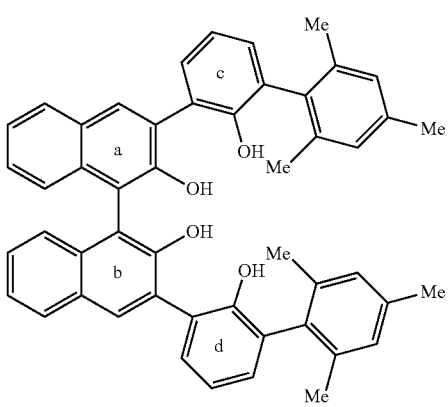

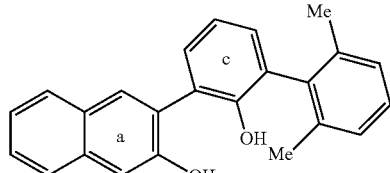
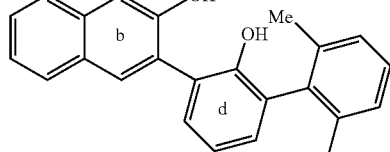
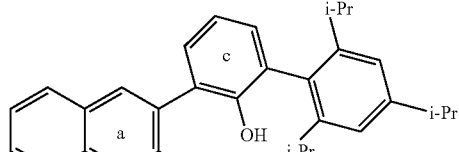
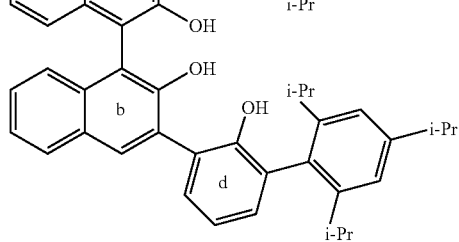

The compounds (n) may be commercially available or may be appropriately produced.

On the other hand, examples of the phosphorylating agents used in the production of the inventive bis-phosphate compounds include phosphorus oxyhalides such as phosphorus oxychloride and phosphorus oxybromide, phosphorus halides such as phosphorus (III) chloride and phosphorus (III) bromide, dihalogenophosphites such as allyl dichlorophosphite and methyl dichlorophosphite, and thiophosphoryl halides such as thiophosphoryl chloride and thiophosphoryl bromide. These phosphorylating agents may be used singly, or two or more kinds may be used in appropriate combination.

The amounts of the compound (n) and the phosphorylating agent used are not particularly limited and are variable in accordance with, for example, the kinds of the compound (n) and the phosphorylating agent used. However, the amount of the phosphorylating agent used is appropriately selected generally from the range of about 2 to 10 equivalent amounts, and preferably about 2.5 to 4 equivalent amounts relative to the compound (n) that is the substrate.

The production of the inventive bis-phosphate compound may be carried out in the presence of a base as required. Examples of the bases include inorganic bases and organic bases. Examples of the inorganic bases include potassium carbonate, potassium hydroxide, lithium hydroxide, sodium hydrogencarbonate, sodium carbonate, potassium hydrogencarbonate, sodium hydroxide, magnesium carbonate and calcium carbonate. Examples of the organic bases include salts of alkali or alkaline earth metals such as potassium naphthalenide, sodium acetate, potassium acetate, magnesium acetate and calcium acetate, organic amines such as triethylamine, diisopropylethylamine, N,N-dimethylaniline, pyridine, 4-dimethylaminopyridine, 1,5-diazabicyclo[4.3.0]non-5-ene, 1,8-diazabicyclo[5.4.0]undec-7-ene, tri-n-butylamine and N-methylmorpholine, metal hydrides such as sodium hydride and potassium hydride, organometallic compounds such as methylmagnesium bromide, ethylmagnesium bromide, propylmagnesium bromide, methyllithium, ethyllithium, propyllithium, n-butyllithium and tert-butyllithium, and quaternary ammonium salts. These may be used singly, or two or more kinds may be used in appropriate combination.

The amount of the base used is not particularly limited and is variable in accordance with, for example, the kind of the base as well as the kinds of the compound (n) and the phosphorylating agent used. However, the amount is appropriately selected generally from the range of about 1 to 5 equivalent amounts, and preferably about 1.5 to 2.5 equivalent amounts per expected equivalent amount of an acid that is generated.

The production of the inventive bis-phosphate compound may be carried out in the presence of a solvent as required. Examples of the solvents include aliphatic hydrocarbons such as pentane, hexane, heptane, octane, decane and cyclohexane, aromatic hydrocarbons such as benzene, toluene and xylene, halogenated hydrocarbons such as dichloromethane, 1,2-dichloroethane, chloroform, carbon tetrachloride and o-dichlorobenzene, ethers such as diethyl ether, diisopropyl ether, tert-butyl methyl ether, dimethoxyethane, ethylene glycol diethyl ether, tetrahydrofuran, 1,4-dioxane and 1,3-dioxolane, ketones such as aceton, methyl ethyl ketone, methyl isobutyl ketone and cyclohexanone, esters such as methyl acetate, ethyl acetate, n-butyl acetate and methyl propionate, amides such as formamide, N,N-dimethylformamide and N,N-dimethylacetamide, sulfoxides such as dimethylsulfoxide, cyano-containing organic compounds such as acetonitrile, and N-methylpyrrolidone. These solvents may be used singly, or two or more kinds may be used in appropriate combination.

The amount of the solvent used is not particularly limited and is variable in accordance with, for example, the kind of the solvent as well as the kinds of the compound (n) and the phosphorylating agent used. However, the amount is appropriately controlled such that the concentration of the compound (n) that is the substrate is usually in the range of about 0.1 to 5 mol/L, and preferably about 0.1 to 1 mol/L.

In addition to the base and the solvent described above, the production of the inventive bis-phosphate compound may involve the addition of other components to the reaction system as required. Further, the production of the inventive bis-phosphate compound may be carried out in the base without using the solvent.

The production of the inventive bis-phosphate compound may be carried out in an inert gas atmosphere as required. One, or two or more inert gases such as nitrogen gas and argon gas may be used.

The temperature of the reaction between the compound (n) and the phosphorylating agent is appropriately selected generally from the range of about 0° C. to 150° C., and preferably about 0 to 80° C. The reaction time is appropriately selected generally from the range of about 10 minutes to 10 days, and preferably about 1 hour to 7 days.

The bis-phosphate compound obtained by the above reaction may be used as an asymmetric reaction catalyst directly or after being subjected to a treatment such as post treatment, purification or separation as required. Specific examples of the means for the treatments such as post treatment, purification and separation include means that are known per se such as solvent extraction, liquidity transformation, solvent change, salting out, crystallization, recrystallization and various chromatographic techniques.

[8] Use

The inventive bis-phosphate compound represented by General Formula (1), in particular the optically active bis-phosphate compound having axial chirality, may be used as an effective catalyst in various asymmetric reactions such as asymmetric Mannich reactions, asymmetric aza-ene type reactions, asymmetric hetero Diels-Alder reactions, asymmetric Friedel-Crafts reactions or asymmetric Diels-Alder reactions.

For example, the compound may be used as an effective catalyst to catalyze an asymmetric Diels-Alder reaction between an amidodiene and an unsaturated aldehyde compound to produce an amidoaldehyde which is useful as a product such as a medicine, an agricultural chemical or a chemical product as well as a synthesis intermediate for such a product.

Preferably, an amidodiene and an unsaturated aldehyde compound may be reacted in the presence of the optically active bis-phosphate compound of the invention represented by General Formula (1) to give an optically active amidoaldehyde. In this reaction, the amounts of the amidodiene and the unsaturated aldehyde compound used are not particularly limited and are variable in accordance with, for example, the kinds of the amidodiene, the unsaturated aldehyde compound and the optically active bis-phosphate compound of General Formula (1) used. However, the amount of the unsaturated aldehyde compound used is appropriately selected generally from the range of about 0.9 to 2.0 equivalent amounts, and preferably about 1.0 to 1.5 equivalent amounts relative to the amidodiene.

Examples of the amidodienes used for the reaction include 1-(methoxycarbonylamino)butadiene, 1-(ethoxycarbonylamino)butadiene, 1-(n-propyloxycarbonylamino)butadiene, 1-(2-propyloxycarbonylamino)butadiene, 1-(n-butyloxycarbonylamino)butadiene, 1-(2-butyloxycarbonylamino)butadiene, 1-(t-butyloxycarbonylamino)butadiene, 1-(benzyloxycarbonylamino)butadiene, 1-(allyloxycarbonylamino)butadiene, 1-(2,2,2-trichloroethoxycarbonylamino)butadiene, 1-(2,2,2-trimethylsilylethoxycarbonylamino)butadiene and analogues of these compounds.

On the other hand, examples of the unsaturated aldehyde compounds include acrolein, methacrolein, 2-ethylacrolein, 2-methyl-2-butenal, 3-methyl-2-butenal, 2-methyl-2-pentenal, crotonaldehyde, 2-ethyl-2-crotonaldehyde, 2-hexenal, citral, cinnamaldehyde and analogues of these compounds.

The above reaction may be carried out in the presence of a solvent as required. Any solvents that do not inhibit the reaction may be used. Examples include aliphatic hydrocarbons such as pentane, hexane, heptane, octane, decane and cyclohexane, aromatic hydrocarbons such as benzene, toluene and xylene, halogenated hydrocarbons such as dichloromethane, 1,2-dichloroethane, chloroform, deuterated chloroform, carbon tetrachloride and o-dichlorobenzene, ethers such as diethyl ether, diisopropyl ether, tert-butyl methyl ether, cyclopentyl methyl ether, dimethoxyethane, ethylene glycol diethyl ether, tetrahydrofuran, 1,4-dioxane and 1,3-dioxolane, ketones such as acetone, deuterated acetone, methyl ethyl ketone, methyl isobutyl ketone and cyclohexanone, tertiary alcohols such as tert-butanol, esters such as methyl acetate, ethyl acetate, n-butyl acetate and methyl propionate, amides such as formamide, N,N-dimethylformamide and N,N-dimethylacetamide, sulfoxides such as dimethylsulfoxide and deuterated dimethylsulfoxide (such as dimethylsulfoxide-$d_6$), cyano-containing organic compounds such as acetonitrile, and N-methylpyrrolidone. These solvents may be used singly, or two or more kinds may be used in appropriate combination.

When the solvent is used, the amount thereof used is variable in accordance with, for example, the kind of the solvent as well as the kinds of the amidodiene and the unsaturated aldehyde compound used, and therefore may be appropriately selected in accordance with the reaction. Usually, the amount of the solvent used may be controlled such that the concentration of the amidodiene, which is the substrate, or the unsaturated aldehyde compound is in the range of about 0.01 to 1 mol/L, and preferably about 0.05 to 0.5 mol/L.

The above reaction may be carried out in an air atmosphere or an inert gas atmosphere. One, or two or more inert gases such as nitrogen gas and argon gas may be used. The pressure conditions may be appropriately selected and the pressure may be normal pressure, increased pressure or reduced pressure.

The reaction temperature is appropriately selected generally from the range of about −100 to 100° C., preferably about −80 to 50° C., and more preferably −80° C. to near room temperature. The reaction time is appropriately selected generally from the range of about 10 minutes to 10 days, and preferably about 1 hour to 7 days.

The optically active amidoaldehyde obtained by the above reaction may be subjected to a treatment such as post treatment, purification or separation as required. The thus-obtained amidoaldehyde is useful as, for example, an intermediate for a product such as a medicine or an agricultural chemical.

Further, the inventive bis-phosphate compound represented by General Formula (1), in particular the optically active bis-phosphate compound having axial chirality, may be used in various asymmetric reactions, for example reactions described in Non Patent Literature 1 such as asymmetric Mannich reactions, asymmetric aza-ene type reactions, asymmetric hetero Diels-Alder reactions, asymmetric Friedel-Crafts reactions or asymmetric Diels-Alder reactions.

For example, the compound may be used as an effective catalyst to catalyze a reaction between an electrophilic compound and a nucleophilic compound to produce an addition compound which is useful as a product such as a medicine, an agricultural chemical or a chemical product as well as a synthesis intermediate for such a product.

Examples of the electrophilic compounds used for the reaction include imines, hemiaminals, enamines, glyoxylates, vinyl ethers and analogues of these compounds.

On the other hand, examples of the nucleophilic compounds include unsaturated aldehydes, 1,3-diketones, silyl ketene acetals, furans, indols, diazoacetates, enamines, azalactones and analogues of these compounds.

Examples of the addition compounds as reaction products include amidoaldehydes, aminodiketones, β-amino acid derivatives, aminomethylfurans, aminomethylindols, α-diazo-β-amino acid derivatives, aziridines, β-iminoamines, piperidines, 1,3-diamines, γ-imino-α-hydroxy esters, β-alkoxy-α-amino acid esters and analogues of these compounds.

Further, the inventive compound may be used as an effective catalyst in the production of a β-aminoaldehyde, which is useful as a product such as a medicine, an agricultural chemical or a chemical product as well as a synthesis intermediate for such a product, from an O-vinyl-hemiaminal compound obtainable from an O-allyl-hemiaminal compound.

Furthermore, the inventive compound may be used as an effective catalyst in the production of a cyclic compound useful as a product such as a medicine, an agricultural chemical or a chemical product as well as a synthesis intermediate for such a product, from a diene compound and an electron deficient, multiple bond compound.

Examples of the electron deficient, multiple bond compounds include glyoxals such as glyoxal, methylglyoxal, ethylglyoxal and phenylglyoxal, glyoxylates such as methyl glyoxylate and ethyl glyoxylate, pyruvic aldehyde and analogues of these compounds.

For example, an imine represented by General Formula (2) below and a 1,3-diketone represented by General Formula (3) below may be reacted with each other in the presence of the optically active bis-phosphate compound of the invention represented by General Formula (1) to give an optically active β-aminoketone represented by General Formula (4) below.

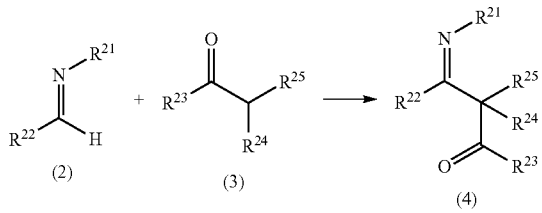

In General Formulae (2) and (4), $R^{21}$ represents a hydrogen atom or a protective group, and $R^{22}$ represents a group having no α-proton or an unsaturated hydrocarbon group. In detail, $R^{21}$ is preferably a hydrogen atom, an acetyl group, a benzoyl group, a tert-butoxycarbonyl group, a benzyloxycarbonyl group, a fluorenylmethoxycarbonyl group or a 2,2,2-trichloroethoxycarbonyl group. $R^{22}$ is preferably a phenyl group, a 4-methylphenyl group, a 4-chlorophenyl group, a naphthyl group, a pyridyl group, a tert-butyl group, —CH=CH—CH$_2$, a 1-propynyl group, an acetyl group, a methoxycarbonyl group, an ethoxycarbonyl group or a benzyloxycarbonyl group.

In General Formulae (3) and (4), $R^{23}$ represents a hydrogen atom, an optionally substituted hydrocarbon group, an optionally substituted heterocyclic group, an optionally substituted alkoxy group, an optionally substituted aryloxy group, an optionally substituted aralkyloxy group or a substituted amino group; $R^{24}$ and $R^{25}$ each independently represent a hydrogen atom, an optionally substituted hydrocarbon group, an optionally substituted heterocyclic group, an electron withdrawing group, an optionally substituted alkoxy group, an optionally substituted aryloxy group, an optionally substituted aralkyloxy group, an optionally substituted alkylthio group, an optionally substituted arylthio group, an optionally substituted aralkylthio group or a hydroxyl group; and a pair of $R^{23}$ and $R^{24}$, $R^{23}$ and $R^{25}$, or $R^{24}$ and $R^{25}$ may be linked together to form a ring. In detail, $R^{23}$ is preferably a hydrogen atom, a methyl group, an ethyl group, an isopropyl group, a phenyl group, a 4-methylphenyl group, a 4-chlorophenyl group, a naphthyl group, a pyridyl group, a methoxy group, an ethoxy group, —SMe, —SEt, —NMe or —NEt$_2$. $R^{24}$ is preferably a hydrogen atom, a methyl group, an ethyl group, an isopropyl group, a phenyl group, a 4-methylphenyl group, a 4-chlorophenyl group, a naphthyl group or a pyridyl group. $R^{25}$ is preferably an aldehyde group, an acetyl group, a benzoyl group, a methoxycarbonyl group, an ethoxycarbonyl group, a tert-butoxycarbonyl group, a benzyloxycarbonyl group, —COSMe, —CONH, —CONMe$_2$, —CONEt$_2$, a cyano group, a nitro group, —PO(OMe) or —SOMe$_2$.

The amounts of the imine and the 1,3-diketone used are not particularly limited and are variable in accordance with, for example, the kinds of the imine and the 1,3-diketone used as well as the kind of the optically active bis-phosphate compound. However, the amount of the 1,3-diketone is appropriately selected generally from the range of about 0.9 to 2.0 equivalent amounts, and preferably about 1.0 to 1.5 equivalent amounts relative to the imine.

The above reaction may be carried out in the presence of a solvent as required. Any solvents that do not inhibit the reaction may be used. Specific examples include the solvents used in the reaction of the amidodiene and the unsaturated aldehyde compound described above.

When the solvent is used, the amount thereof used is not particularly limited and is variable in accordance with, for example, the kinds of the imine and the 1,3-diketone used. However, the amount is appropriately selected such that the concentration of the imine is generally in the range of about 0.01 to 1 M, and preferably about 0.05 to 0.2 M.

The above reaction may be carried out in an air atmosphere or an inert gas atmosphere. One, or two or more inert gases such as nitrogen gas and argon gas may be used. The pressure conditions may be appropriately selected and the pressure may be normal pressure, increased pressure or reduced pressure.

The reaction temperature is appropriately selected generally from the range of about −78 to 100° C., preferably about 0 to 50° C., and more preferably near room temperature. The reaction time is appropriately selected generally from the range of about 10 minutes to 10 days, and preferably about 1 hour to 7 days.

The optically active β-aminoketone obtained by the above reaction may be subjected to a treatment such as post treatment, purification or separation as required.

The thus-obtained optically active β-aminoketone is useful as, for example, an intermediate for a product such as a medicine or an agricultural chemical.

Further, for example, an imine represented by General Formula (2) below and a furan represented by General Formula (5) below may be reacted with each other in the presence of the optically active bis-phosphate compound of the invention represented by General Formula (1) to give an optically active furanylamine represented by General Formula (6) below.

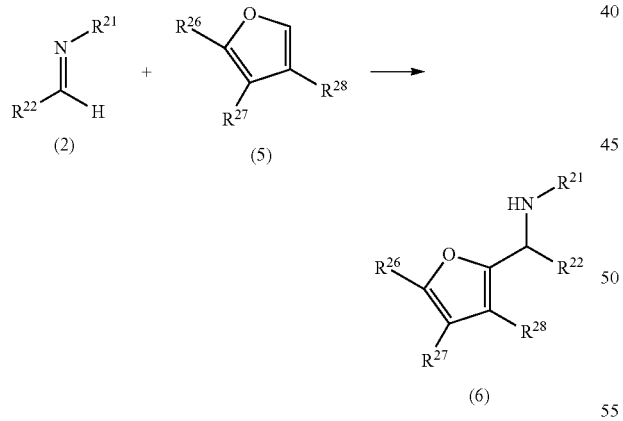

In General Formulae (2) and (6), $R^{21}$ and $R^{22}$ are the same as those described above.

In General Formulae (5) and (6), $R^{26}$ to $R^{28}$ each independently represent a hydrogen atom, an optionally substituted alkoxy group, an optionally substituted aryloxy group, an optionally substituted aralkyloxy group or an optionally substituted hydrocarbon group. Examples thereof include those described hereinabove.

Preferred examples of the furans represented by General Formula (5) include 2-methoxyfuran, 2-ethoxyfuran, 2-methylfuran, 2-ethylfuran, 2-propylfuran and 2-(2-propyl)furan.

The amounts of the imine and the furan used are not particularly limited and are variable in accordance with, for example, the kinds of the imine and the furan used as well as the kind of the optically active bis-phosphate compound. However, the amount of the furan is appropriately selected generally from the range of about 0.9 to 5.0 equivalent amounts, and preferably about 1.0 to 3.0 equivalent amounts relative to the imine.

The above reaction may be carried out in the presence of a solvent as required. Any solvents that do not inhibit the reaction may be used. Specific examples include the solvents used in the reaction of the amidodiene and the unsaturated aldehyde compound described above.

When the solvent is used, the amount thereof used is not particularly limited and is variable in accordance with, for example, the kinds of the imine and the furan used. However, the amount is appropriately selected such that the concentration of the imine is generally in the range of about 0.01 to 1 M, and preferably about 0.05 to 0.5 M.

The above reaction may be carried out in an air atmosphere or an inert gas atmosphere. One, or two or more inert gases such as nitrogen gas and argon gas may be used. The pressure conditions may be appropriately selected and the pressure may be normal pressure, increased pressure or reduced pressure.

Regarding the reaction temperature, the reaction temperature is appropriately selected generally from the range of about −50 to 100° C., preferably about −20 to 50° C., and more preferably near room temperature. The reaction time is appropriately selected generally from the range of about 10 minutes to 10 days, and preferably about 30 minutes to 7 days.

The optically active furanylamine obtained by the above reaction may be subjected to a treatment such as post treatment, purification or separation as required.

The thus-obtained optically active furanylamine is useful as, for example, an intermediate for a product such as a medicine or an agricultural chemical.

Furthermore, for example, an imine represented by General Formula (2) above and a carbamate represented by General Formula (7) below may be reacted with each other in the presence of the optically active bis-phosphate compound of the invention represented by General Formula (1) to give an optically active β-aminoketone.

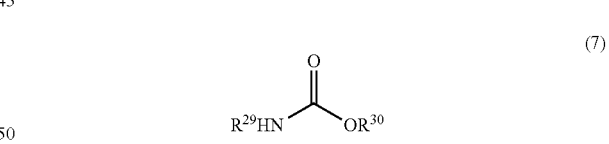

In General Formula (7), $R^{29}$ represents a hydrogen atom or an optionally substituted hydrocarbon group such as alkyl group, alkenyl group, alkynyl group or aryl group; $R^{30}$ represents an optionally substituted hydrocarbon group such as alkyl group, alkenyl group, alkynyl group or aryl group; and $R^{29}$ and $R^{30}$ may be linked together to form a ring. Preferably, $R^{29}$ and $R^{30}$ represent groups similar to those represented by $R^1$ to $R^{14}$ in General Formula (1).

The amounts of the imine and the carbamate used are not particularly limited and are variable in accordance with, for example, the kinds of the imine and the carbamate used as well as the kind of the optically active bis-phosphate compound. However, the amount of the carbamate is appropriately selected generally from the range of about 0.9 to 5.0 equivalent amounts, and preferably about 1.0 to 3.0 equivalent amounts relative to the imine.

The above reaction may be carried out in the presence of a solvent as required. Any solvents that do not inhibit the reaction may be used. Specific examples include the solvents used in the reaction of the amidodiene and the unsaturated aldehyde compound described above.

When the solvent is used, the amount thereof used is not particularly limited and is variable in accordance with, for example, the kinds of the imine and the carbamate used. However, the amount is appropriately selected such that the concentration of the imine is generally in the range of about 0.01 to 1 M, and preferably about 0.05 to 0.5 M.

The above reaction may be carried out in an air atmosphere or an inert gas atmosphere. One, or two or more inert gases such as nitrogen gas and argon gas may be used. The pressure conditions may be appropriately selected and the pressure may be normal pressure, increased pressure or reduced pressure.

Regarding the reaction temperature, the reaction temperature is appropriately selected generally from the range of about −50 to 100° C., preferably about −20 to 50° C., and more preferably near room temperature. The reaction time is appropriately selected generally from the range of about 10 minutes to 10 days, and preferably about 30 minutes to 7 days.

The optically active β-aminoketone obtained by the above reaction may be subjected to a treatment such as post treatment, purification or separation as required.

The thus-obtained optically active β-aminoketone is useful as, for example, an intermediate for a product such as a medicine or an agricultural chemical.

EXAMPLES

The present invention will be described in greater detail by presenting examples hereinbelow. However, the invention is not limited by the following examples within the spirit of the invention. In the specification including the following examples, "Me" represents methyl group, "i-Pr" isopropyl group, "Cbz" benzyloxycarbonyl group, "Boc" tert-butoxycarbonyl group, "Ph" phenyl group, "Bz" benzoyl group, and "M" mol/L.

Example 1

Synthesis 1 of bis-phosphate

A bis-phosphate was synthesized according to the following reaction formula.

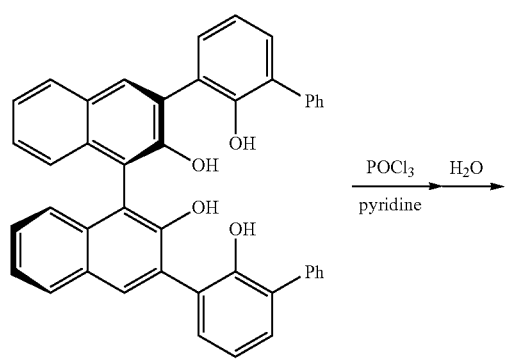

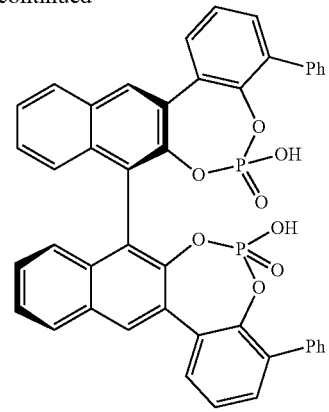

In a nitrogen atmosphere, 8.0 mL of dehydrated pyridine was added to 498 mg (0.80 mmol) of tetraphenol synthesized based on J. Am. Chem. Soc. 1998, 120(28), p. 6920-6930. After the mixture was stirred for some time at room temperature, 367 µL (4.0 mmol) of phosphoryl chloride was added. Thereafter, the reaction temperature was increased to 70° C., and stirring was performed for 24 hours. After the reaction solution was naturally cooled, 8.0 mL of water was added thereto. The mixture was stirred at 70° C. for 12 hours. After the reaction solution was naturally cooled, it was diluted with 30 mL of dichloromethane, and 20 mL of 6 M hydrochloric acid was added. The solvent was distilled away under reduced pressure, and the residue was dissolved in 15 mL of methanol. Concentrated hydrochloric acid was added. The mixture was stirred at room temperature for 1 hour. Thereafter, the target compound was extracted with dichloromethane and was dried with anhydrous sodium sulfate. After the solvent was distilled away under reduced pressure, the residue was purified by silica gel column chromatography (dichloromethane:methanol (volume ratio)=100/1, Merck Silica gel 60 extra pure), thereby obtaining 119 mg (0.13 mmol, yield 16%) of a bis-phosphate as a white solid.

$^1$H NMR (DMSO, 500 MHz) δ (ppm): 8.37 (s, 2H), 8.15 (d, 2H), 7.92 (t, 2H), 7.71 (d, 4H), 7.54 (t, 6H), 7.39 (t, 6H), 7.32 (t, 2H), 7.17 (d, 2H), 3.95 (brs).

Example 2

Synthesis 2 of bis-phosphate

A bis-phosphate was obtained (yield 18%) as a white solid according to the following reaction formula in the same manner as in EXAMPLE 1.

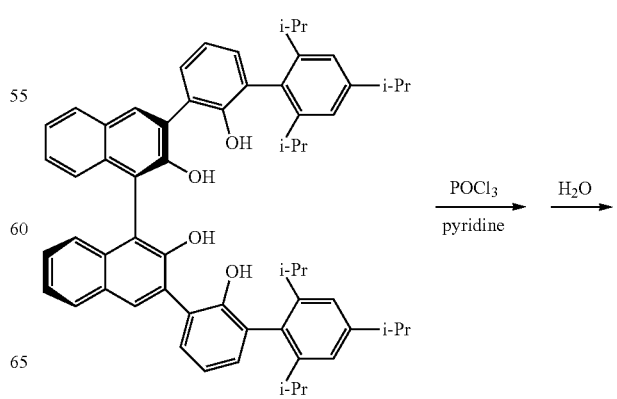

-continued

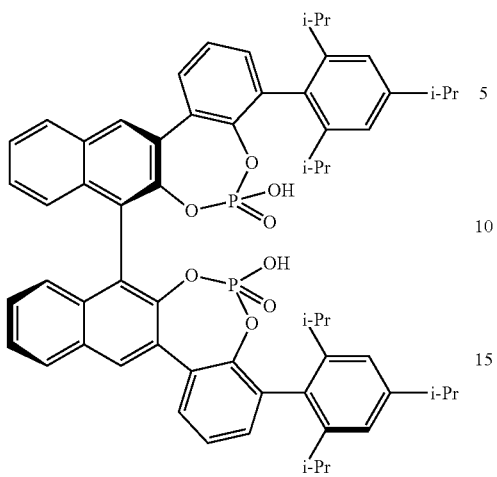

¹H NMR (DMSO, 500 MHz) δ (ppm): 8.43 (s, 1H), 8.14 (d, 1H, J=8.1 Hz), 7.90 (d, 1H, J=7.7 Hz), 7.52 (t, 1H, J=7.5 Hz), 7.44 (t, 1H, J=7.7 Hz), 7.38 (t, 1H, J=7.7 Hz), 7.22 (d, 1H, J=7.7 Hz), 7.16 (d, 1H, J=8.5 Hz), 7.01 (s, 1H), 6.95 (s, 1H), 3.77 (brs), 2.86 (m, 1H), 2.69 (m, 1H), 2.29 (m, 1H), 1.21 (d, 6H, J=6.8 Hz), 1.06 (d, 6H, J=6.8 Hz), 0.98 (d, 3H, J=6.8 Hz), 0.82 (d, 3H, J=6.8 Hz).

Example 3

Asymmetric Diels-Alder Reaction 1

An amidoaldehyde was produced according to the following reaction formula using the bis-phosphate synthesized in EXAMPLE 1 as a catalyst.

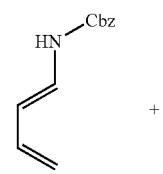

Amidodiene (I)

+

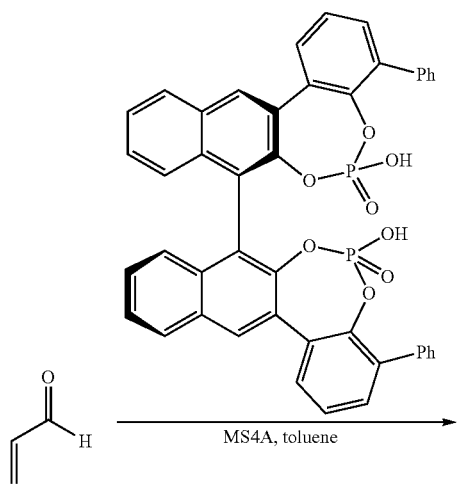

-continued

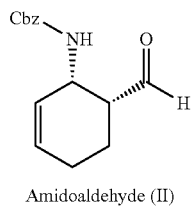

Amidoaldehyde (II)

The amidodiene (I) (benzylbutane-1,3-dienyl carbamate) as a reaction substrate was synthesized in accordance with Org. Synth. Coll. 1988, Vol. 6, p. 95.

A reaction container was provided which contained 3.7 mg (0.005 mmol) of the bis-phosphate synthesized in EXAMPLE 1 and 150 mg of MS 4A (molecular sieve 4A). In a nitrogen atmosphere, 0.50 mL of toluene and subsequently 20 µL (0.3 mmol) of acrolein were added to the container. The mixture was stirred at room temperature. Thereafter, the reaction container was cooled to −78° C. A toluene solution of the amidodiene (I) (40.6 mg (0.20 mmol) of amidodiene (I)/0.50 mL of toluene) was slowly added dropwise, and stirring was performed at −80° C. for 48 hours. A saturated aqueous sodium hydrogencarbonate solution was added to the reaction solution, and further ethyl acetate was added to perform extraction. The extraction layer was sequentially washed with a saturated aqueous sodium hydrogencarbonate solution and a saturated salt solution, and was dried with anhydrous sodium sulfate. After the solvent was distilled away under reduced pressure, the residue was purified by silica gel column chromatography (hexane:ethyl acetate (volume ratio)= 15/1→8/1), thereby obtaining 37.7 mg (0.146 mmol, yield 73%, 90% e.e., (1s, 6R)) of the target amidoaldehyde (II) as a colorless liquid.

¹H NMR (CDCl₃, 500 MHz) δ (ppm): 9.81 (s, 1H), 7.37-7.30 (m, 5H), 5.86-5.84 (m, 1H), 5.71-5.68 (m, 1H), 5.11-5.038 (m, 3H), 4.74 (brs, 1H), 2.79-2.77 (m, 1H), 2.09-2.05 (m, 2H), 2.00-1.96 (m, 1H), 1.77-1.74 (m, 1H). HPLC (Hexane:EtOH=95:5, 0.6 ml/min, Chiralcel OD-H); major enantiomer t$_r$=35.6 min, minor enantiomer t$_r$=24.1 min.

Example 4

Asymmetric Diels-Alder Reaction 2

An amidoaldehyde was produced according to the following reaction formula in the same manner as in EXAMPLE 3 using the bis-phosphate synthesized in EXAMPLE 2 as a catalyst.

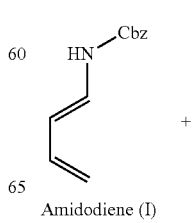

Amidodiene (I)

+

-continued

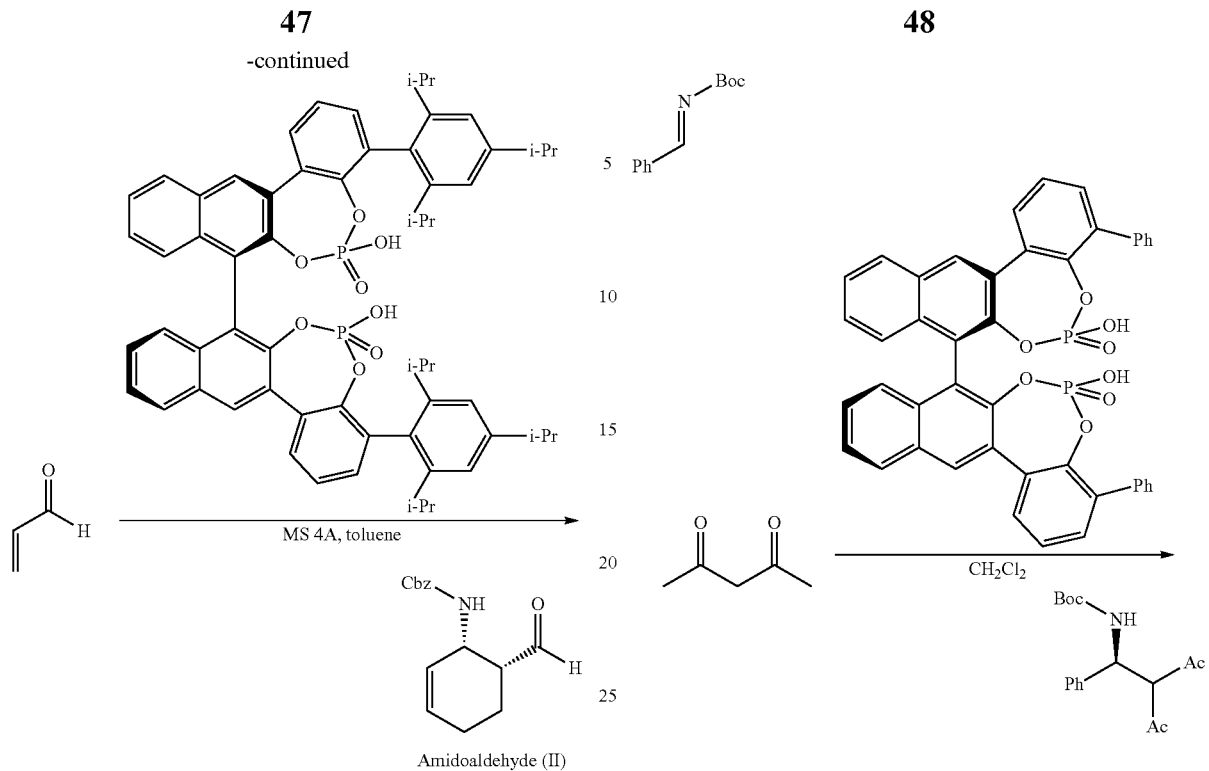

Amidoaldehyde (II)

A reaction container was provided which contained 5.0 mg (0.005 mmol) of the bis-phosphate synthesized in EXAMPLE 2 and 150 mg of MS 4A (molecular sieve 4A). In a nitrogen atmosphere, 0.50 mL of toluene and subsequently 20 µL (0.3 mmol) of acrolein were added to the container. The mixture was stirred at room temperature. Thereafter, the reaction container was cooled to −78° C. A toluene solution of the amidodiene (I) (40.6 mg (0.20 mmol) of amidodiene (I)/0.50 mL of toluene) was slowly added dropwise, and stirring was performed at −80° C. for 48 hours. A saturated aqueous sodium hydrogencarbonate solution was added to the reaction solution, and further ethyl acetate was added to perform extraction. The extraction layer was sequentially washed with a saturated aqueous sodium hydrogencarbonate solution and a saturated salt solution, and was dried with anhydrous sodium sulfate. After the solvent was distilled away under reduced pressure, the residue was purified by silica gel column chromatography (hexane:ethyl acetate (volume ratio)= 15/1→8/1), thereby obtaining 37.7 mg (0.158 mmol, yield 79%, 90% e.e., (1S,6R)) of the target amidoaldehyde (II) as a colorless liquid.

$^1$H NMR (CDCl$_3$, 500 MHz) δ (ppm): 9.81 (s, 1H), 7.37-7.30 (m, 5H), 5.86-5.84 (m, 1H), 5.71-5.68 (m, 1H), 5.11-5.038 (m, 3H), 4.74 (brs, 1H), 2.79-2.77 (m, 1H), 2.09-2.05 (m, 2H), 2.00-1.96 (m, 1H), 1.77-1.74 (m, 1H). HPLC (Hexane:EtOH=95:5, 0.6 ml/min, Chiralcel OD-H); major enantiomer t$_r$=35.6 min, minor enantiomer t$_r$=24.1 min.

Example 5

Asymmetric Mannich Reaction (Mannich Reaction)

A β-aminoketone was produced according to the following reaction formula using a bis-phosphate illustrated below as a catalyst which had been synthesized in the same manner as in EXAMPLE 1.

The imine ((E)-t-butylbenzylidene carbamate) as a reaction substrate was synthesized in accordance with J. Am. Chem. Soc. 2002, Vol. 124, p. 12964-12965.

A reaction container was provided which contained 1.4 mg (0.002 mmol) of the bis-phosphate synthesized in accordance with the method of EXAMPLE 1. In a nitrogen atmosphere, 2 mL of dichloromethane and subsequently 41.0 mg (0.2 mmol) of the imine and 22 µL (0.22 mmol) of acetylacetone were added to the container. The mixture was stirred at room temperature for 1 hour. The reaction mixture was purified by silica gel column chromatography (dichloromethane:ether (volume ratio)=20/1), thereby obtaining 54.8 mg (0.18 mmol, yield 90%, 5% e.e., (S)) of the target β-aminoketone as a white solid.

$^1$H NMR (CDCl$_3$, 270 MHz) δ (ppm): 7.20-7.34 (m, 5H), 5.73 (br, 1H), 5.46 (br, 1H), 4.18 d, J=6.8 Hz, 1H), 2.17 (brs, 3H), 2.09 (s, 3H), 1.37 (s, 9H).

HPLC (Hexane:EtOH=90:10, 1.0 ml/min, Chiralpak AD-H); major enantiomer t$_r$=13.8 min, minor enantiomer t$_r$=17.4 min.

Example 6

Asymmetric Friedel-Crafts Reaction (Friedel-Crafts Reaction)

A furanylamine was produced according to the following reaction formula using a bis-phosphate illustrated below as a catalyst which had been synthesized in the same manner as in EXAMPLE 1.

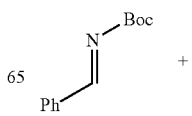

-continued

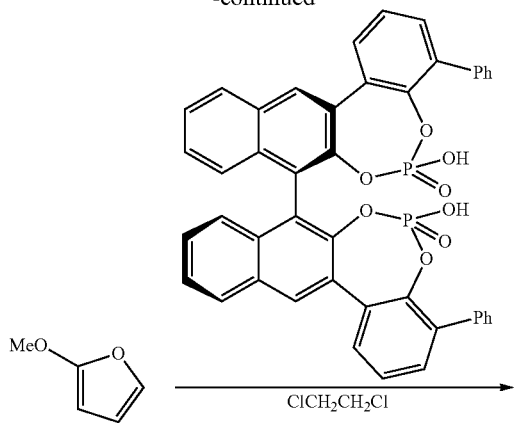

The imine ((E)-t-butylbenzylidene carbamate) as a reaction substrate was synthesized in accordance with J. Am. Chem. Soc. 2002, Vol. 124, p. 12964-12965.

A reaction container was provided which contained 1.4 mg (0.002 mmol) of the bis-phosphate synthesized in the same manner as in EXAMPLE 1. In a nitrogen atmosphere, 2 mL of dichloroethane and subsequently 41.0 mg (0.2 mmol) of the imine and 22 μL (0.22 mmol) of methoxyfuran were added to the container. The mixture was stirred at −35° C. for 24 hours. The reaction mixture was purified by silica gel column chromatography (hexane:ethyl acetate (volume ratio)=12/1→8/1), thereby obtaining 48.5 mg (0.16 mmol, yield 80%, 16% e.e., (S)) of the target furanylamine as a white solid.

$^1$H NMR (CDCl$_3$, 270 MHz) δ (ppm): 7.23-7.38 (m, 5H), 5.94 (d, J=3.1 Hz, 1H), 5.79 (br, 1H), 5.24 (br, 1H), 5.04 (d, J=3.1 Hz, 1H), 3.80 (s, 1H), 1.43 (brs, 9H).

HPLC (Hexane:i-PrOH=95:5, 1.0 ml/min, Chiralpak AD-H); major enantiomer t$_r$=18.0 min, minor enantiomer t$_r$=14.9 min.

Example 7

Asymmetric Aza-Ene Type Reaction (Aza-Ene type Reaction)

A β-aminoketone was produced according to the following reaction formula using a bis-phosphate illustrated below as a catalyst which had been synthesized in the same manner as in EXAMPLE 1.

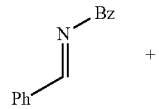

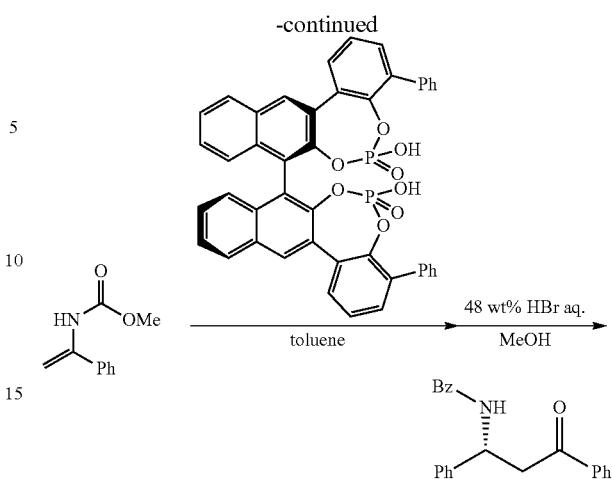

The enecarbamate (methyl 1-phenylvinylcarbamate) as a reaction substrate was synthesized in accordance with Bull. Chem. Soc. Chim. Fr. 1965, Vol. 5, p. 1454-1457.

A reaction container was provided which contained 1.4 mg (0.002 mmol) of the bis-phosphate synthesized in the same manner as in EXAMPLE 1 and 41.8 mg (0.2 mmol) of the imine. In a nitrogen atmosphere, a solution of 42.6 mg (0.24 mmol) of the enecarbamate in toluene (2 ml) was added to the container. The mixture was stirred at room temperature for 5 hours. Thereafter, a saturated aqueous sodium hydrogencarbonate solution was added to the reaction solution to terminate the reaction. The obtained reaction solution was extracted with dichloromethane. The extracted organic layer was dried with anhydrous sodium sulfate. The anhydrous sodium sulfate was filtered off, and the solvent was distilled away using an evaporator under reduced pressure. The obtained crude product was dissolved in methanol (4 mL), and a 48 wt % aqueous hydrogen bromide solution was added. The reaction solution was stirred at room temperature for 5 minutes, and a saturated aqueous sodium hydrogencarbonate solution was added at 0° C., thereby terminating the reaction. The temperature was naturally increased to room temperature. Extraction was performed with dichloromethane, and the organic layer was dried with anhydrous sodium sulfate. The anhydrous sodium sulfate was filtered off, and the solvent was distilled away using an evaporator under reduced pressure. The crude product was purified by silica gel column chromatography (hexane:ethyl acetate (volume ratio)=8/1→1/1), thereby obtaining 56.0 mg (0.12 mmol, yield 85%, 52% e.e., (R)) of the β-aminoketone as a white solid.

$^1$H NMR (CDCl$_3$, 270 MHz) δ (ppm): 7.87 (dd, J=8.4, 1.4 Hz, 2H), 7.79 (dd, J=8.4, 1.6 Hz, 2H), 7.62 (d, J=8.0 Hz, 1H), 7.52 (tt, J=7.6, 1.6 Hz, 1H), 7.33-7.47 (m, 7H), 7.15-7.29 (m, 3H), 5.73 (dt, J=8.0, 5.4 Hz, 1H), 3.83 (dd, J=16.9, 5.4 Hz, 1H), 3.47 (dd, J=16.9, 5.4 Hz, 1H).

HPLC (Hexane:i-PrOH=80:20, 1.0 ml/min, Chiralpak AD-H); major enantiomer t$_r$=23.2 min, minor enantiomer t$_r$=30.7 min.

The present invention has been described in detail based on specific embodiments. However, it is apparent to those skilled in the art that various modifications can be made without departing from the spirit and scope of the invention.

The present invention is based on a Japanese Patent Application filed on Mar. 9, 2010 (Japanese Patent Application No. 2010-051973), the entire content of which is incorporated herein by reference.

The invention claimed is:

1. A bis-phosphate compound comprising a tetraaryl skeleton of formula (1):

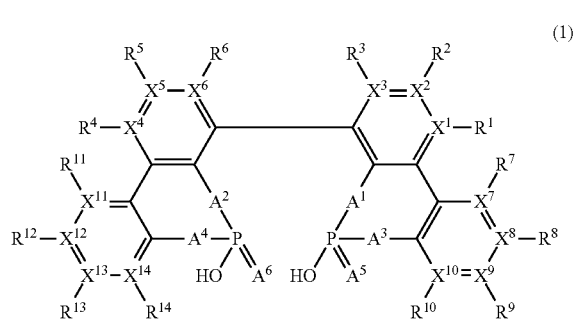

wherein:
- $R^1$ to $R^{14}$ are each independently a hydrogen atom, an optionally substituted hydrocarbon group, an optionally substituted heterocyclic group, a hydroxyl group, an optionally substituted alkoxy group, an optionally substituted aryloxy group, an optionally substituted acyl group, an optionally substituted alkoxycarbonyl group, an optionally substituted aryloxycarbonyl group, an optionally substituted carbamoyl group, an optionally substituted alkylthiocarbonyl group, an optionally substituted arylthiocarbonyl group, a carboxyl group, an optionally substituted alkylthio group, an optionally substituted arylthio group, an optionally substituted amino group, a substituted silyl group, or a halogen atom; in any combination of $R^1$ to $R^{14}$, these substituents may be linked together to form a ring;
- $X^1$ to $X^{14}$ are each independently a carbon atom or a nitrogen atom, wherein in the case of a nitrogen atom, there is no substituent on the nitrogen atom;
- $A^1$ to $A^6$ are each independently an oxygen atom or a sulfur atom; and
- the —OH group in the phosphate moiety may form a metal salt, an ammonium salt, or an amine salt.

2. The bis-phosphate compound of claim 1, wherein the bis-phosphate compound is optically active.

3. The bis-phosphate compound of claim 2, wherein the bis-phosphate compound is optically active due to axial chirality.

4. A process, comprising:
performing an asymmetric reaction in the presence of an optically active bis-phosphate compound of claim 2.

5. The process of claim 4, wherein an amidodiene and an unsaturated aldehyde compound are reacted with each other in the presence of the optically active bis-phosphate compound, to produce an optically active amidoaldehyde.

6. The process of claim 4, wherein an imine and a 1,3-diketone are reacted with each other in the presence of the optically active bis-phosphate compound, to produce an optically active β-aminoketone.

7. The process of claim 4, wherein an imine and a furan are reacted with each other in the presence of the optically active bis-phosphate compound, to produce an optically active furanylamine.

8. The process of claim 4, wherein an imine and a carbamate are reacted with each other in the presence of the optically active bis-phosphate compound, to produce an optically active β-aminoketone.

9. A method for producing a bis-phosphate compound of claim 1, the method comprising:
reacting a compound of formula (N) with a phosphorylating agent:

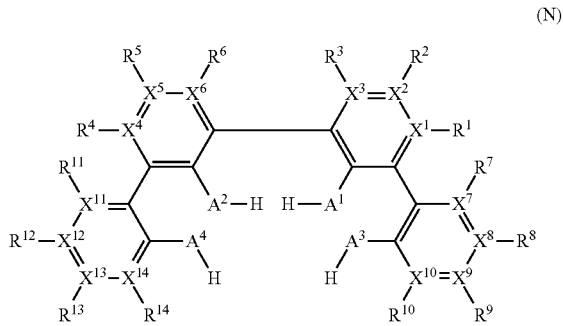

wherein:
- $R^1$ to $R^{14}$ are each independently a hydrogen atom, an optionally substituted hydrocarbon group, an optionally substituted heterocyclic group, a hydroxyl group, an optionally substituted alkoxy group, an optionally substituted aryloxy group, an optionally substituted acyl group, an optionally substituted alkoxycarbonyl group, an optionally substituted aryloxycarbonyl group, an optionally substituted carbamoyl group, an optionally substituted alkylthiocarbonyl group, an optionally substituted arylthiocarbonyl group, a carboxyl group, an optionally substituted alkylthio group, an optionally substituted arylthio group, an optionally substituted amino group, a substituted silyl group or a halogen atom; in any combination of $R^1$ to $R^{14}$, these substituents may be linked together to form a ring;
- $X^1$ to $X^{14}$ are each independently a carbon atom or a nitrogen atom, wherein in the case of a nitrogen atom, there is no substituent on the nitrogen atom; and
- $A^1$ to $A^4$ are each independently an oxygen atom or a sulfur atom.

10. The method of claim 9, wherein the phosphorylating agent is at least one selected from the group consisting of a phosphorus oxyhalide, a phosphorus halide, a dihalogenophosphine, and a thiophosphoryl halide.

11. A process, comprising:
performing an asymmetric reaction in the presence of an optically active bis-phosphate compound of claim 3.

12. The process of claim 11, wherein an amidodiene and an unsaturated aldehyde compound are reacted with each other in the presence of the optically active bis-phosphate compound, to produce an optically active amidoaldehyde.

13. The process of claim 11, wherein an imine and a 1,3-diketone are reacted with each other in the presence of the optically active bis-phosphate compound, to produce an optically active β-aminoketone.

14. The process of claim 11, wherein an imine and a furan are reacted with each other in the presence of the optically active bis-phosphate compound, to produce an optically active furanylamine.

15. The process of claim 11, wherein an imine and a carbamate are reacted with each other in the presence of the optically active bis-phosphate compound, to produce an optically active β-aminoketone.

16. The method of claim 9, wherein the phosphorylating agent is a phosphorus oxyhalide.

17. The method of claim 9, wherein the phosphorylating agent is a phosphorus halide.

18. The method of claim 9, wherein the phosphorylating agent is a dihalogenophosphine.

19. The method of claim 9, wherein the phosphorylating agent is a thiophosphoryl halide.

* * * * *